United States Patent
Nishihara

(10) Patent No.: US 6,675,646 B2
(45) Date of Patent: Jan. 13, 2004

(54) LIQUID-QUANTITY MONITORING APPARATUS AND LIQUID-CONSUMING APPARATUS WITH THE SAME

(75) Inventor: Yuichi Nishihara, Nagano-Ken (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 10/106,826

(22) Filed: Mar. 27, 2002

(65) Prior Publication Data

US 2002/0144550 A1 Oct. 10, 2002

(30) Foreign Application Priority Data

Mar. 28, 2001 (JP) ........................ 2001-093446

(51) Int. Cl.$^7$ .................. G01M 25/56; G01N 5/02
(52) U.S. Cl. ............. 73/290 V; 73/290 V; 73/149; 73/52; 73/1.48; 73/1.73; 73/651; 347/7
(58) Field of Search ................. 73/290 V, 149, 73/52, 290 R, 1.48, 1.73, 651; 347/7

(56) References Cited

U.S. PATENT DOCUMENTS

| | | | | |
|---|---|---|---|---|
| 4,644,789 A | * | 2/1987 | Snyder | 73/290 V |
| 5,235,844 A | * | 8/1993 | Bonne et al. | 73/24.01 |
| 6,161,420 A | * | 12/2000 | Dilger et al. | 73/24.01 |
| 6,470,744 B1 | * | 10/2002 | Usui et al. | 73/290 R |

FOREIGN PATENT DOCUMENTS

JP 2001-146030 5/2001

\* cited by examiner

Primary Examiner—Hezron Williams
Assistant Examiner—André K. Jackson
(74) Attorney, Agent, or Firm—Sughrue Mion, PLLC

(57) ABSTRACT

A liquid-quantity monitoring apparatus includes: a piezoelectric device having a vibrating part capable of being exposed at least partly to a liquid-containing space, the piezoelectric device being capable of vibrating the vibrating part by a given drive signal and of generating a signal representing back electromotive force generated by vibration of the vibrating part; and a liquid-quantity determining unit for determining a quantity of liquid remaining in the liquid-containing space, to which the vibrating part is exposed, based on a resonance frequency of a residual vibration signal output from the piezoelectric device due to a residual vibration of the vibrating part after the vibrating part has been vibrated by the drive signal. The liquid-quantity determining unit counts a number of pulses included in the residual vibration signal, measures a time period necessary for counting a predetermined number of pulses after starting counting the pulses, and determines the quantity of the liquid based on the time period measured. The liquid-quantity determining unit repeats a pulse-counting operation for counting the predetermined number of pulses with different starting time points, and decides that a measurement is incorrect when differences between the time periods are greater than a predetermined allowable limit.

23 Claims, 14 Drawing Sheets

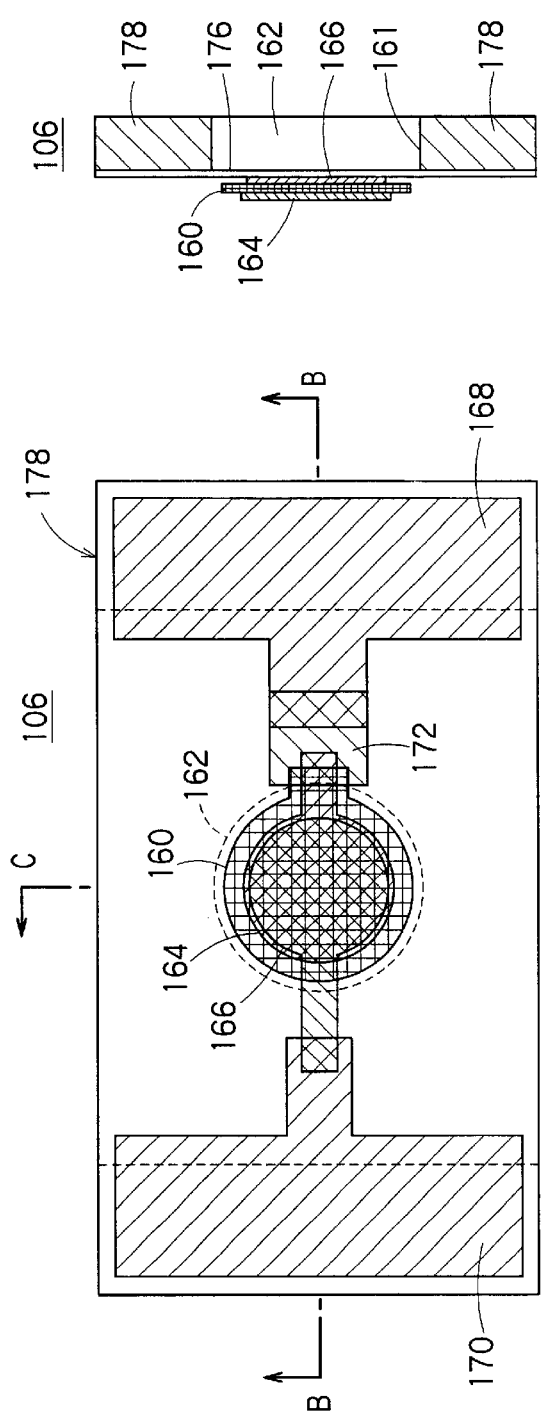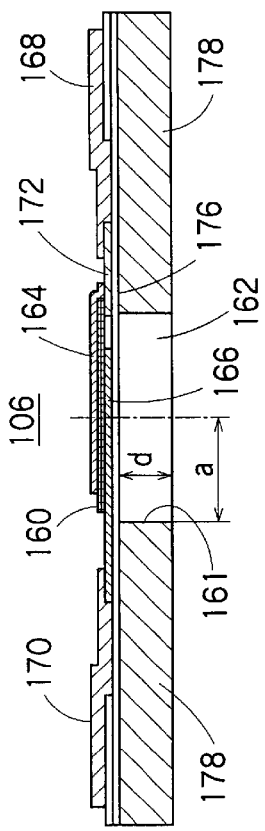

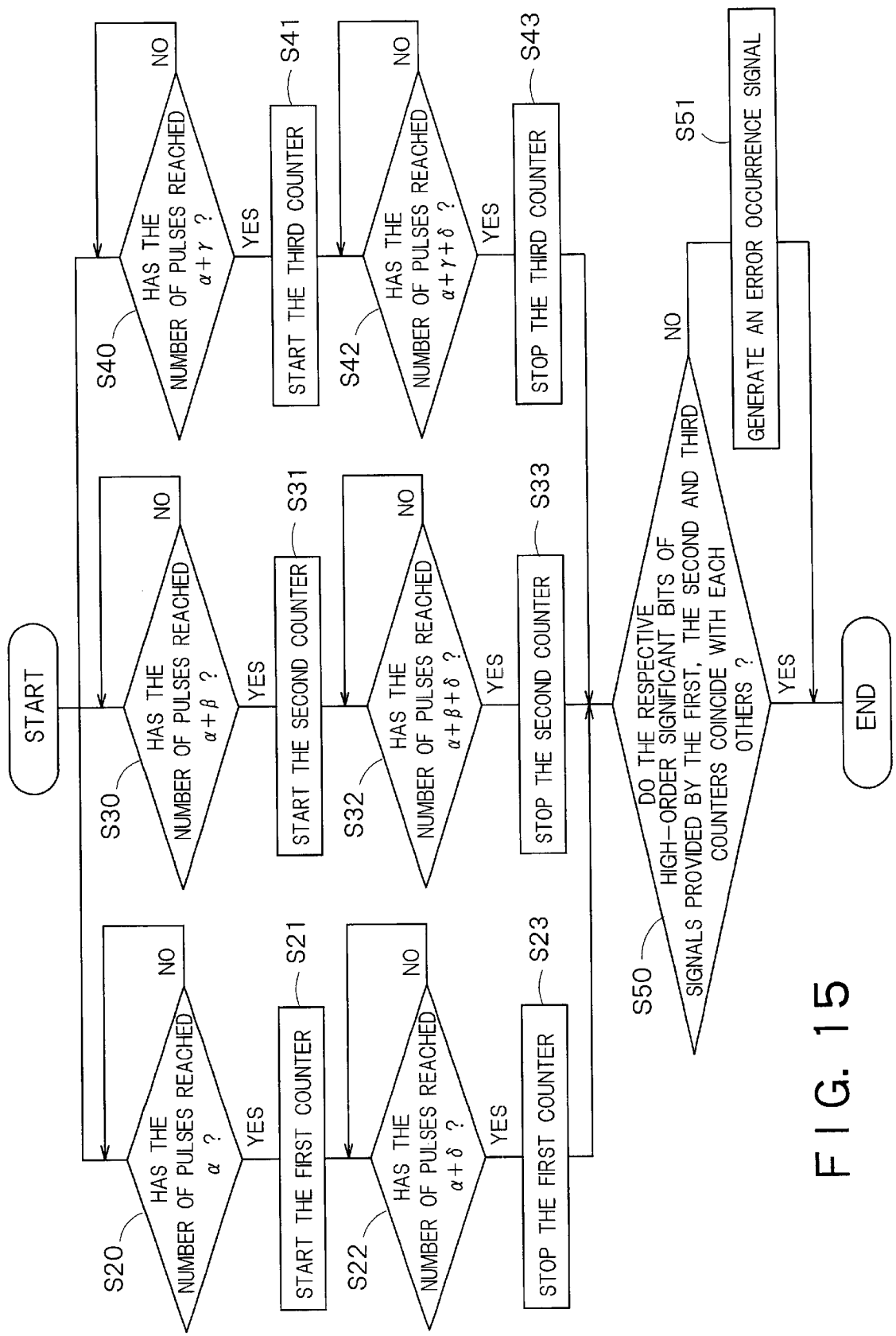
F I G. 15

LIQUID-QUANTITY MONITORING APPARATUS AND LIQUID-CONSUMING APPARATUS WITH THE SAME

BACKGROUND OF THE INVENTION

1. Field of the Invention

The present invention relates to a liquid-quantity monitoring apparatus and a liquid-consuming apparatus provided with the same. More particularly, the present invention relates to a liquid-quantity monitoring apparatus employing a piezoelectric device to monitor the quantity of a liquid, and a liquid-consuming apparatus provided with the liquid-quantity monitoring apparatus.

2. Description of the Related Art

An ink-jet recording apparatus as an example of a liquid-consuming apparatus has an ink-jet recording head provided with pressure producing means for producing pressure in pressure chambers, and nozzles for jetting the pressurized ink in ink drops, and a carriage mounted with the ink-jet recording head.

In the ink-jet recording apparatus, the ink contained in an ink tank (ink cartridge) is supplied continuously through an ink supply passage into the ink-jet recording head during a printing operation. The ink tank is, for example, a replaceable ink cartridge that can be easily replaced with a new one by the user when the ink contained therein is exhausted.

A conventional ink consumption managing method of managing the consumption of the ink contained in the ink cartridge accumulates the number of ink drops jetted by the ink-jet recording head and the quantity of the ink sucked during maintenance work by software, and calculates ink consumption. Another conventional ink consumption managing method uses a level measuring electrode placed in an ink cartridge to determine a time point when ink consumption reaches a predetermined quantity.

The conventional ink consumption managing method of managing ink consumption by accumulating the number of ink drops jetted by the ink-jet recording head and the quantity of the ink sucked during maintenance work by the software has the following problem. Ink drops jetted by some ink-jet recording head have different weights, respectively. Although such ink drops respectively having different weights do not affect image quality significantly, the ink cartridge should be filled with a quantity of ink including a margin to compensate for an error in the cumulative ink consumption due to the use of ink drops respectively having different weights. Consequently, some ink remains in some of ink cartridges after the ink cartridge has been judged to be exhausted.

The conventional ink consumption managing method using the level measuring electrode to determine a time point when ink consumption reaches a predetermined quantity is able to measure the quantity of actually consumed ink, and hence is capable of managing the quantity of the remaining ink with high reliability. However, this method is applicable to managing the quantity of limited kinds of inks because the measurement of the level of the ink relies on the electric conductivity of the ink, and requires a complicated sealing structure for sealing the electrode. A noble metal having high electrical conductivity and high corrosion-resistant property and used for forming the electrode increases the manufacturing cost of the ink cartridge. Since this method needs two electrodes, the ink cartridge needs increased manufacturing steps and an increased manufacturing cost.

A piezoelectric device is proposed to solve the foregoing problems. This piezoelectric device is incorporated into a liquid container. A measuring means capable of accurately measuring the level of ink is proposed. The measuring means includes a means for estimating ink consumption on the basis of the number of jetted ink drops and a piezoelectric device for measuring actual ink consumption.

Those techniques measure the quantity of ink on the basis of a residual vibration signal generated by the residual vibrations of a vibrating part of the piezoelectric device. However, the amplitude of the residual vibration signal is small and hence the measurement is affected significantly by noise and hence it is possible that the quantity of ink cannot be accurately measured.

SUMMARY OF THE INVENTION

The present invention has been made in view of the foregoing circumstances and it is therefore an object of the present invention to provide a liquid-quantity monitoring apparatus capable of monitoring the quantity of a liquid contained in a liquid container with high reliability, and a liquid consuming apparatus provided with the liquid quantity monitoring system.

According to a first aspect of the present invention, a liquid-quantity monitoring apparatus comprises: a piezoelectric device having a vibrating part capable of being exposed at least partly to a liquid-containing space for containing a liquid, the piezoelectric device being capable of vibrating the vibrating part by a given drive signal and of generating a signal representing back electromotive force generated by vibration of the vibrating part; and liquid-quantity determining means for determining a quantity of the liquid remaining in the liquid-containing space, to which the vibrating part is exposed, based on a resonance frequency of a residual vibration signal which is output from the piezoelectric device due to a residual vibration of the vibrating part after the vibrating part has been vibrated by the drive signal. The liquid-quantity determining means counts a number of pulses included in the residual vibration signal, measures a time period necessary for counting a predetermined number of pulses after starting counting the pulses, and determines the quantity of the liquid based on the time period which has been measured. The liquid-quantity determining means repeats a pulse-counting operation for counting the predetermined number of pulses with different starting time points, and decides that a measurement is incorrect when differences between the time periods measured by the pulse-counting operations are greater than a predetermined allowable limit.

Preferably, the pulse-counting operation is repeated at least three times. The starting time points when the pulse-counting operation is to be started for first, second and third pulse-counting cycles are so determined that a time period necessary for counting the predetermined number of pulses in the first pulse-counting cycle and a time period necessary for counting the predetermined number of pulses in the third pulse-counting cycle do not overlap each other, and a time period necessary for counting the predetermined number of pulses in the second pulse-counting cycle overlaps the time periods necessary for counting the predetermined number of pulses in the first and the third pulse-counting cycles.

Preferably, the liquid-quantity determining means measures again the time periods each necessary for counting the predetermined number of pulses when the measurement is judged to be incorrect.

Preferably, the liquid is contained in an ink container for an ink-jet recording head, the piezoelectric device being combined with the ink container such that at least part of the vibrating part of the piezoelectric device is exposed to an ink chamber formed in the ink container. The liquid-quantity determining means measures again the time periods each necessary for counting the predetermined number of pulses while a carriage holding the ink-jet recording head is stopped, when the measurement is judged to be incorrect.

Preferably, the liquid-quantity determining means measures again the time periods each necessary for counting the predetermined number of pulses while an ink jetting operation of the ink-jet recording head is stopped, when the measurement is judged to be incorrect.

Preferably, the liquid is contained in an ink container for an ink-jet recording head, the piezoelectric device being combined with the ink container with at least a part of the vibrating unit thereof exposed to an ink chamber formed in the ink container. The liquid-quantity determining means measures again the time periods each necessary for counting the predetermined number of pulses while an ink jetting operation of the ink-jet recording head is stopped, when the measurement is judged to be incorrect.

Preferably, the liquid-quantity determining means is capable of deciding whether or not a level of the liquid passed a position where the vibrating part is positioned, based on a change of a resonance frequency of the residual vibration signal that occurs when the level of the liquid passes the vibrating unit.

According to the second aspect of the present invention, a liquid consuming apparatus comprises: the liquid-quantity monitoring apparatus mentioned above; a liquid container combined with the piezoelectric device of the liquid-quantity monitoring apparatus; and a liquid consuming unit that consumes a liquid supplied from the liquid container.

According to the third aspect of the present invention, a computer readable recording medium storing a program to be executed by a computer system including at least one computer to realize functions of the liquid-quantity determining means of the liquid-quantity monitoring apparatus mentioned above.

BRIEF DESCRIPTION OF THE DRAWINGS

FIGS. 1A, 1B and 1C are a plan view, and sectional views, respectively, of an actuator (piezoelectric device) included in a liquid-quantity monitoring apparatus in a preferred embodiment according to the present invention;

FIG. 15 is a flow chart of a counting procedure to be executed in step S3 of the liquid-quantity determining procedure shown in FIG. 14.

DESCRIPTION OF THE PREFERRED EMBODIMENTS

A liquid-quantity monitoring apparatus in a preferred embodiment according to the present invention and an ink-jet recording apparatus provided with the liquid-quantity monitoring apparatus will be described with reference to the accompanying drawings.

FIGS. 1A, 1B, 1C and 2 show an actuator 106, i.e., a piezoelectric device, employed in a liquid-quantity monitoring apparatus in a preferred embodiment according to the present invention, and equivalent circuits of the actuator 106. The actuator 106 senses the change of acoustic impedance through the measurement of the resonance frequency of a residual vibration to estimate the consumption of a liquid contained in an ink container.

Figure 2:
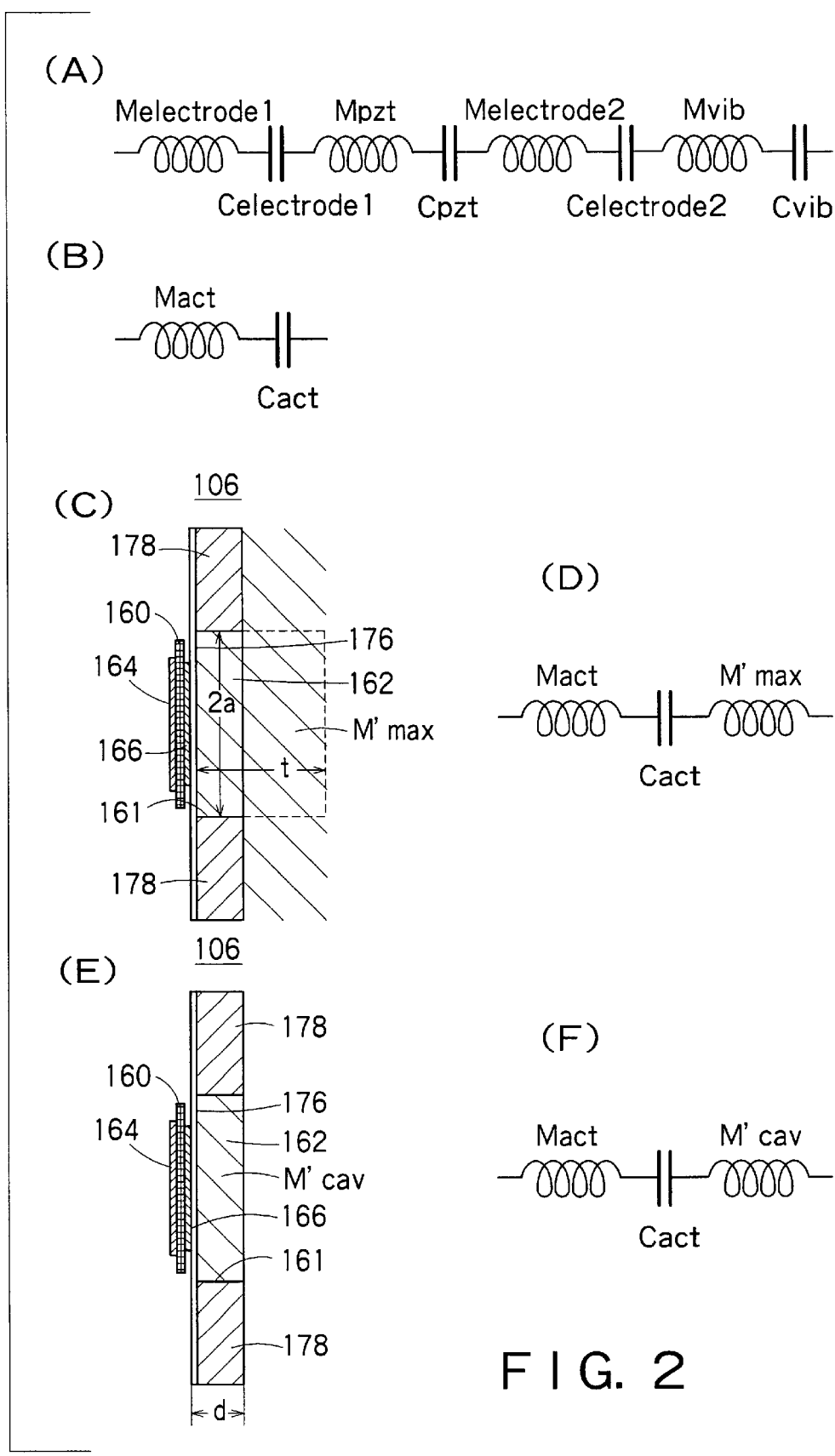
FIGS. 2, (A), (B), (C), (D), (E) and (F) are circuit diagrams of equivalent circuits and sectional end views of peripheral parts of the actuator.

FIG. 1A is an enlarged plan view of the actuator 106, FIG. 1B is a sectional view taken on line B—B in FIGS. 1A, FIG. 1C is a sectional view taken on line C—C in FIG. 1A, FIG. 2, (A) and (B) are circuit diagrams of an equivalent circuit of the actuator 106, FIG. 2, (C) and (D) are a sectional view and a circuit diagram of an equivalent circuit, respectively, of the actuator 106 and peripheral parts in a state where an ink cartridge is full, and FIG. 2, (E) and (F) are a sectional view and a circuit diagram an equivalent circuit, respectively, of the actuator 106 and peripheral parts in a state where the ink cartridge is empty.

The actuator 106 comprises a substrate 178 provided with a circular opening 161 in its substantially central part, a diaphragm 176 placed on the upper surface, i.e., a first major surface, of the substrate 178 so as to cover the opening 161, a piezoelectric layer 160 placed on the diaphragm 176, an upper electrode 164 attached to the upper surface of the piezoelectric layer 160, a lower electrode 166 attached to the lower surface of the piezoelectric layer 160, an upper-electrode terminal 168 electrically connected to the upper electrode 164, a lower-electrode terminal 170 electrically connected to the lower electrode 166, and an auxiliary electrode 172 disposed between and electrically connecting the upper electrode 164 and the upper-electrode terminal 168.

The piezoelectric layer 160, the upper electrode 164 and the lower electrode 166 have circular main parts, respectively. The circular main parts of the piezoelectric layer 160, the upper electrode 164 and the lower electrode 166 form an actuator, i.e., a piezoelectric device.

The diaphragm 176 is put on the upper surface of the substrate 178 so as to cover the opening 161, a part of the diaphragm 176 corresponding to the opening 161 and the side surface of the opening 161 of the substrate 178, i.e., a cavity forming member, define a cavity 162. The lower surface, i.e., a second major surface, of the substrate 178 faces an ink container, so that the cavity 162 is exposed to a liquid (ink) contained in the ink container. The diaphragm 176 is attached closely to the substrate 178 in a liquid-tight fashion to prevent the liquid from leaking from the cavity 162 onto the upper surface of the substrate 178.

The lower electrode 166 is contiguous with the upper surface of the diaphragm 176. The circular main part of the lower electrode 166 is substantially aligned with the opening 161. The circular main part of the lower electrode 166 is smaller than that of the opening 161.

The piezoelectric layer 160 is formed on the upper surface of the lower electrode 166 with its circular main part substantially aligned with the opening 161. The area of the circular main part of the piezoelectric layer 160 is smaller than that of the opening 161 and is greater than that of the circular main part of the lower electrode 166.

The upper electrode 164 is placed on the upper surface of the piezoelectric layer 160 with its circular main part substantially aligned with the opening 161. The area of the circular main part of the upper electrode 164 is smaller than those of the respective circular main parts of the piezoelectric layer 160 and the opening 161 and is greater than that of the circular main part of the lower electrode 166.

Thus the circular main part of the piezoelectric layer 160 is sandwiched between the respective circular main parts of the upper electrode 164 and the lower electrode 166, so that the piezoelectric layer 160 can be effectively driven for warping. The respective circular main parts of the piezoelectric layer 160, the upper electrode 164 and the lower electrode 166 form the piezoelectric element of the actuator 106.

The piezoelectric element is contiguous with the diaphragm 176. The area of the opening 161 is larger than those of the respective circular main parts of the piezoelectric layer 160, the upper electrode 164 and the lower electrode 166. Therefore a vibrating section that vibrates actually of the diaphragm 176 is dependent on the opening 161.

Since the respective areas of the respective circular main parts of the upper electrode 164, the piezoelectric layer 160 and the lower electrode 166 are smaller than that of the opening 161, the diaphragm is able to vibrate easily.

Since the circular main part electrically connected to the piezoelectric layer 160 of the lower electrode 166 is smaller than that of the upper electrode 164, a part that has a piezoelectric effect of the piezoelectric layer 160 is dependent on the circular main part of the lower electrode 166.

The respective circular main parts of the piezoelectric layer 160, the upper electrode 164 and the lower electrode 166 forming the piezoelectric element are substantially aligned with the opening 161. The center of the circular opening 161 determining the vibrating section of the diaphragm 176 coincides substantially with the center of the actuator 106. Thus the center of the vibrating part of the actuator 106 coincides substantially with the center of the actuator 106.

Since the principal part of the piezoelectric element and the vibrating section of the diaphragm 176 are circular, the vibrating part of the actuator 106 is symmetrical with respect to the center of the actuator 106.

Therefore, unnecessary vibrations attributable to structural asymmetry are not produced and hence resonance frequency can be measured accurately.

The actuator 106 having the vibrating part symmetrical with respect to the center of the actuator 106 is easy to fabricate, differences in shape between piezoelectric elements can be reduced, and hence differences in resonance frequency between piezoelectric elements are small.

Since the vibrating part has an isotropic shape, the actuator 106 is easy to attach to the ink container and can be satisfactorily attached to the ink container.

The amplitude of a waveform of back electromotive force, and the difference in amplitude between vibrations at a resonance frequency in a state where the ink container contains the liquid and vibrations at a resonance frequency in a state where the ink container is empty can be augmented to improve the accuracy of resonance frequency measurement by increasing the area of the circular vibrating section of the diaphragm 176.

The vibrational strain of the diaphragm 176 is greater than that of the substrate 178. That is, the actuator 106 includes a two-layer structure consisting of the substrate 178 having low compliance, i.e., a member resistant to straining, and the diaphragm 176 having high compliance, i.e., a member subject to straining. The substrate 178 of the two-layer structure can be firmly fixed to the ink container, while the diaphragm 176 can be greatly strained. Therefore, the amplitude of a waveform of back electromotive force, and the difference in amplitude between vibrations at a resonance frequency in a state where the ink container contains the liquid and vibrations at a resonance frequency in a state where the ink container is empty are large and hence the accuracy of resonance frequency measurement can be improved.

Since the diaphragm 176 has high compliance, the attenuation of vibrations is delayed, which improves the accuracy of resonance frequency measurement.

The node of vibration of the actuator 106 is in the vicinity of a peripheral part of the cavity 162, i.e., the edge of the opening 161.

The upper-electrode terminal 168 is formed on the upper surface of the diaphragm 176 and is electrically connected to the upper electrode 164 by the auxiliary electrode 172. The lower-electrode terminal 170 is formed on the upper surface of the diaphragm 176 so as to be electrically connected to the lower electrode 166. Since the upper electrode 164 is formed on the upper surface of the piezoelectric layer 160, the lower surface of the upper electrode 164 is at a height equal to the sum of the respective thicknesses of the piezoelectric layer 160 and the lower electrode 166 from the upper surface of the diaphragm 176. It is difficult form the upper electrode 164 having sections at such different levels. Even if the upper electrode 164 having sections at such different levels could be formed, the upper electrode 164 cannot be satisfactorily connected to the upper electrode terminal 168 and it is possible that the upper electrode 164 is cut. Therefore, the upper electrode 164 is electrically connected to the upper-electrode terminal 168 by the auxiliary electrode 172. Thus, the both the piezoelectric layer 160 and the upper electrode 164 are supported on the auxiliary electrode 172, which ensures a desired mechanical strength for the actuator 106 and the reliable connection of the upper electrode 164 and the upper-electrode terminal 168.

The piezoelectric element and a part corresponding to the piezoelectric element of the diaphragm 176 form the vibrating part of the actuator 106. Preferably, the components of the actuator 106 are combined integrally by baking. The actuator 106 formed in a single unit is easy to handle.

Increase in the strength of the substrate 178 improves the vibrating characteristic of the actuator 106. When the substrate 178 has a high strength, only the vibrating part of the actuator 106 vibrates and the rest of the parts of the actuator 106 do not vibrate. Parts other than the vibrating part of the actuator 106 can be prevented from vibrating by forming the piezoelectric element of the actuator 106 in a small thickness and a small size and to form the diaphragm 176 in a small thickness in addition to the enhancement of the strength of the substrate 178.

Materials suitable for forming the piezoelectric layer 160 include lead zirconate titanate (PZT), lead lanthanum zirconate titanate (PLZT) and leadless piezoelectric substances. Materials suitable for forming the substrate 178 include zirconia and alumina. Preferably, the diaphragm 176 and the substrate 178 are formed of the same material. The upper electrode 164, the lower electrode 166, the upper-electrode terminal 168 and the lower-electrode terminal 170 are formed of a conductive material, such as gold, silver, copper, platinum aluminum nickel or such.

The actuator 106 can be attached to the liquid container, such as an ink cartridge for an ink-jet recording apparatus, i.e., a liquid consuming apparatus, or a container containing a cleaning liquid for cleaning a recording head.

The actuator 106 shown in FIGS. 1A, 1B, 1C and 2 is attached to the ink container such that the cavity 162 is opened to the liquid contained in the ink container; that is, at least a part of the vibrating part of the actuator 106 is exposed to a space in the ink container. When the ink container is in a state where the ink container is filled with the liquid (ink), the cavity 162 and a space surrounding the cavity is filled up with the liquid.

When the ink container is in a state where the liquid contained in the ink container is consumed and the level of the liquid contained in the ink container drops below a level corresponding to the actuator 106, the cavity 162 is empty or some of the liquid remains only in the cavity 162 and the space around the cavity is filled with air.

The actuator 106 measures the difference at least in acoustic impedance between those states. Thus, the actuator 106 is able to discriminate between the state where the ink container contains a sufficient quantity of the liquid and the state where a predetermined quantity of the liquid contained in the ink container has been consumed.

The principle of the measurement of the liquid quantity by the actuator 106 will be described hereinafter.

The actuator 106 is capable of measuring the variation of the acoustic impedance of the liquid through the measurement of the variation of the resonance frequency. The resonance frequency can be determined through the measurement of back electromotive force produced by residual vibrations of the vibrating part following the vibration of the vibrating part of the actuator 106. The piezoelectric element generates back electromotive force by the residual vibration of the vibrating part of the actuator 106. The magnitude of the back electromotive force is dependent on the amplitude of the vibration of the vibrating part of the actuator 106. Therefore, the greater the amplitude of the vibration of the vibrating part of the actuator 106, the easier is the measurement of the back electromotive force. The period of variation of the magnitude of the back electromotive force is dependent on the frequency of the residual vibration of the vibrating part of the actuator 106; that is, the frequency of the vibration of the vibrating part of the actuator 106 corresponds to the frequency of the back electromotive force. The resonance frequency is the frequency of the vibration of the vibrating part of the actuator 106 resonant with the vibration of the liquid in contact with the vibrating part.

The vibrating part of the actuator 106 is a part of the diaphragm 176 defining the cavity 162 together with the side wall of the opening 161. In a state where the ink container contains the liquid sufficiently, the cavity 162 is filled up with the liquid and the vibrating part of the actuator 106 is in contact with the liquid contained in the ink container. In a state where the ink container contains the liquid insufficiently, the vibrating part is in contact with the liquid remaining in the ink container or is not in contact with the liquid and is in contact with air or exposed to a vacuum space.

Since the actuator 106 is provided with the cavity 162, the actuator 106 can be designed such that some of the liquid contained in the ink container remains in a region corresponding to the vibrating part of the actuator 106 for the following reasons.

Sometimes, the liquid wets the vibrating part of the actuator 106 despite the level of the liquid contained in the ink container being below a level corresponding to the actuator 106 when the actuator 106 is attached to the ink container at some position in some angular position. If it is decided whether or not any of the liquid still remains in the ink container only on the basis of whether or not any of the liquid remains on the vibrating part of the actuator 106, the liquid wetting the vibrating part of the actuator 106 prevents accurately determining whether or not any of the liquid remains in the ink container.

Suppose that the liquid level is below a level corresponding to the position of the actuator 106. The ink container shakes to undulate the liquid contained in the ink container as a carriage holding the ink container is reciprocated. Consequently, the liquid wets the vibrating part of the actuator 106 and the actuator decides erroneously that the ink container contains the liquid sufficiently.

The actuator 106 of the present invention is provided with the cavity 162 to decide accurately whether or not any of the liquid still remains in the ink container even if the vibrating part is wetted with the liquid. Thus, it is possible to prevent the erroneous operation of the actuator 106 even if the ink container shakes to undulate the liquid. Thus the cavity 162 prevents the actuator 106 from making erroneous operation.

FIG. 2, (E) shows a threshold quantity of the liquid, in which the liquid contained in the ink container has been exhausted and some of the liquid remains in the cavity 162 of the actuator 106. When the space around the cavity 162 does not contain any liquid and the quantity of the liquid in the cavity 162 is smaller than the threshold, it is decided that the liquid has been exhausted. When the space around the cavity 162 contains the liquid and the quantity of the liquid is greater than the threshold quantity, it is decided that the ink container contains the liquid.

Suppose that the actuator 106 is attached to a side wall of the ink container. Then, it is decided that the liquid has been exhausted when the level of the liquid contained in the ink container is below a level corresponding to the actuator 106, and it is decided that some of the liquid remains in the ink container when the level of the liquid contained in the ink container is above the level corresponding to the actuator 106.

It is possible to decide that the liquid has been exhausted with reference to the threshold quantity even in a case where the liquid has dried up and in a case where the carriage shakes and the vibrating part is wetted again with the liquid after the liquid contained in the cavity 162 has been depleted due to the shake of the carriage.

Description will be give of the operation and the principle of determining the condition of the liquid in the ink container on the basis of the resonance frequency at which the vibration of the vibrating part of the actuator 106 resonate with that of the liquid in contact with the vibrating part.

A voltage is applied through the upper-electrode terminal 168 and the lower-electrode terminal 170 across the upper electrode 164 and the lower electrode 166 of the actuator 106. Consequently, an electric field is created in a part of the piezoelectric layer 160 sandwiched between the upper electrode 164 and the lower electrode 166 to strain the piezoelectric layer 160. Consequently, only the vibrating section of the diaphragm 176 is warped for flexural vibration. The flexural vibration of the vibrating part of the actuator 106 continues for a period of time after the piezoelectric layer 16 is strained.

The residual vibration is the free vibration of the vibrating part of the actuator 106 and the liquid. Therefore, the vibrating part and the liquid can be easily resonated by applying voltage of a pulse waveform or a rectangular waveform to the piezoelectric electric layer 160. The residual vibration is the vibration of the vibrating part of the actuator 106 caused by the deformation of the piezoelectric layer 160, and hence the piezoelectric layer 160 generates back electromotive force. The back electromotive force can be measured through the upper electrode 164, the lower electrode 166, the upper-electrode terminal 168 and the lower-electrode terminal 170. A resonance frequency can be specified on the basis of the measured back electromotive force. The quantity of the liquid contained in the ink container can be determined on the basis of the resonance frequency. Generally, resonance frequency $f_s$ is expressed by $$f_s = 1/\{2\pi(M \cdot C_{act})^{1/2}\} \quad (1)$$

where M is the sum of the inertance $M_{act}$ and additional inertance M', and $C_{act}$ is the compliance of the vibrating part.

FIG. 1C is a sectional view of the actuator 106 in a state where any liquid does not remain in the cavity 162 and FIGS. 2, (A) and (B) are circuit diagrams of equivalent circuits of the vibrating part and the cavity, respectively, of the actuator 106 in a state where any liquid does not remain in the cavity 162.

The inertance $M_{act}$ is equal to the product of the thickness and the density of the vibrating part divided by the area of the vibrating part, which is expressed, as shown in FIG. 2, (A), by:

$$M_{act} = M_{pzt} + M_{electrode1} + M_{electrode2} + M_{vib} \quad (2)$$

where $M_{pzt}$ is the product of the thickness and density of the piezoelectric layer 160 of the vibrating part divided by the area of the piezoelectric layer 160, $M_{electrode1}$ is the product of the thickness and density of the upper electrode 164 divided by the area of the upper electrode 164, $M_{electrode2}$ is the product of the thickness and density of the lower electrode 166 of the vibrating part divided by the area of the lower electrode 166, and $M_{vib}$ is the product of the thickness and density of the vibrating section of the diaphragm 176 divided by the area of the vibrating section of the diaphragm 176.

Although the piezoelectric layer 160, the upper electrode 164, the lower electrode 166, and the vibrating section of the diaphragm 176 have different areas, respectively, it is preferable that the differences in area between them are small to calculate $M_{act}$ on the basis of the thickness, density and area of the composite vibrating part.

Preferably, the sizes of parts of the piezoelectric layer 160, the upper electrode 164 and the lower electrode 166 other than the circular main parts of the same are negligibly small as compared with those of the circular main parts. Thus the inertance $M_{act}$ is equal to the sum of the inertances of the upper electrode 164, the lower electrode 166, the piezoelectric layer 160 and the vibrating section of the diaphragm 176. The compliance $C_{act}$ is equal to the compliance of the vibrating part including the upper electrode 164, the lower electrode 166, the piezoelectric layer 160 and the vibrating section of the diaphragm 176.

FIGS. 2, (A), (B), (D) and (F) are circuit diagrams of respective equivalent circuits of the vibrating part of the actuator 106 and the cavity 162. In those equivalent circuits, $C_{act}$ indicates the compliance of the vibrating part of the actuator 106, and $C_{electrode1}$, $C_{electrode2}$ and $C_{vib}$ indicate the compliances of the piezoelectric layer 160, the upper electrode 164, the lower electrode 166 and the diaphragm 176 of the vibrating part, respectively. The compliance $C_{act}$ is expressed by $$1/C_{act} = (1/C_{pzt}) + (1/C_{electrode1}) + (1/C_{electrode2}) + (1/C_{vib}) \quad (3)$$

It is known from Expressions (2) and (3), the equivalent circuits shown in FIG. 2, (A) can be represented by the equivalent circuit shown in FIG. 2, (B).

The compliance $C_{act}$ corresponds to a volume of the liquid contained in a recess formed in a unit area of a planar member when pressure is applied thereto; that is, the compliance $C_{act}$ indicates readiness to yield.

FIG. 2, (C) is a sectional view of the actuator 106 in a state where the ink container contains the liquid sufficiently and the space around the vibrating part of the actuator 106 is filled up with the liquid. In FIG. 2, (C), M'$_{max}$ indicates maximum additional inertance, i.e., mass affecting the vibration of the vibrating part, divided by the square of the area of the vibrating part in a state where the space around the vibrating part of the actuator 106 is filled up with the liquid.

$$M'_{max} = \{\pi \cdot \rho/(2k^3)\} \cdot \{2(2k \cdot a)^3/(3\pi)\}/(\pi \cdot a^2)^2 \quad (4)$$

where a is the radius of the vibrating part, $\rho$ is the density of the liquid and k is the number of waves.

Expression (4) is defined on an assumption that the vibrating part of the actuator 106 is a circular part of a radius a. Additional inertance M' is a value of an apparent increment in the mass of the vibrating part caused by the liquid surrounding the vibrating part. As obvious from Expression (4), the maximum additional inertance M'$_{max}$ is greatly dependent on the radius a of the vibrating part and the density $\rho$ of the liquid. The number k of waves is expressed by Expression (5).

$$k = 2\pi \cdot f_{act}/c \quad (5)$$

where $f_{act}$ is the resonance frequency of the vibrating part and c is the velocity of sound propagating through the liquid.

FIG. 2, (D) is a circuit diagram of equivalent circuits of the vibrating part and the cavity 162 of the actuator 106 in a state where the ink container is filled up with the liquid and some liquid is left in the space around the vibrating part as shown in FIG. 2, (C).

FIG. 2, (E) is a sectional view of the actuator 106 in a state where the liquid in the ink container is exhausted and any liquid is not left in the space around the vibrating part of the actuator 106, whereas some liquid still remains in the cavity 162 of the actuator 106.

Expression (4) expresses the maximum inertance $M'_{max}$ as a function of the density ρ of the liquid and other parameters in a state where the ink container is filled up with the liquid. The additional inertance M' in a state where the liquid contained in the ink container has been exhausted, some of the liquid remains in the cavity 162, and the liquid in the space around the vibrating part of the actuator 106 has been replaced with air or a vacuum space is expressed by Expression (6).

$$M' = \rho \cdot t / S$$

where t is the thickness of a film of the liquid affecting and S is the area of the vibrating part of the actuator 106. $S = \pi a^2$ when the vibrating part is a circular part of a radius a.

The additional inertance M' is expressed by Expression (4) in a state where the ink container contains the liquid sufficiently, and the space around the vibrating part of the actuator is filled up with the liquid, and is expressed by Expression (6) in a state where the liquid has been exhausted, some of the liquid remains in the cavity 162, and the liquid in the space around the vibrating part of the actuator 106 has been replaced with air or a vacuum space.

Additional inertance $M'_{cav}$ in a state as shown in FIG. 2, (E) where the liquid contained in the ink container has been exhausted, any liquid does not remain around the vibrating part of the actuator 106, and some liquid remains in the cavity 162 of the actuator 106 is discriminated from the maximum additional inertance $M'_{max}$ in a state where the space around the vibrating part of the actuator 106 is filled up with the liquid.

FIG. 2, (F) is a circuit diagram of equivalent circuits of the vibrating part and the cavity 162 of the actuator 106 in a state shown in FIG. 2, (E) where the liquid contained in the ink container has been exhausted, any liquid does not remain around the vibrating part of the actuator 106, and some liquid remains in the cavity 162 of the actuator 106.

As obvious from Expression (6), parameters defining the condition of the liquid are the density ρ of the liquid and the thickness t of the film of the liquid. When the ink container contains the liquid sufficiently, the vibrating part of the actuator is in contact with the liquid. When the ink container contains the liquid insufficiently, some of the liquid remains in the cavity 162 or the vibrating part of the actuator 106 is in contact with air or is exposed to a vacuum space. Transient additional inertance $M'_{var}$ that appears while the additional inertance changes from $M'_{max}$ in the state shown in FIG. 2, (C) to $M'_{cav}$ in the state shown in FIG. 2, (E) as the liquid around the actuator 106 is consumed varies with the variation of the density ρ of the liquid and the thickness t of the film of the liquid depending on the condition of storage of the liquid in the ink container, and hence the resonance frequency $f_s$ varies accordingly. Therefore, the quantity of the liquid contained in the ink container can be estimated through the measurement of the resonance frequency $F_s$.

When t is equal to the thickness d of the vibrating part as shown in FIG. 2, (E), $$M'_{cav} \rho \cdot d / S \qquad (7)$$

Different types of liquids have different compositions and different densities ρ, and hence the additional inertance M' and the resonance frequency $f_s$ change when the liquids are changed. Thus the type of the liquid can be determined through the measurement of the resonance frequency $f_s$.

Figure 3A:
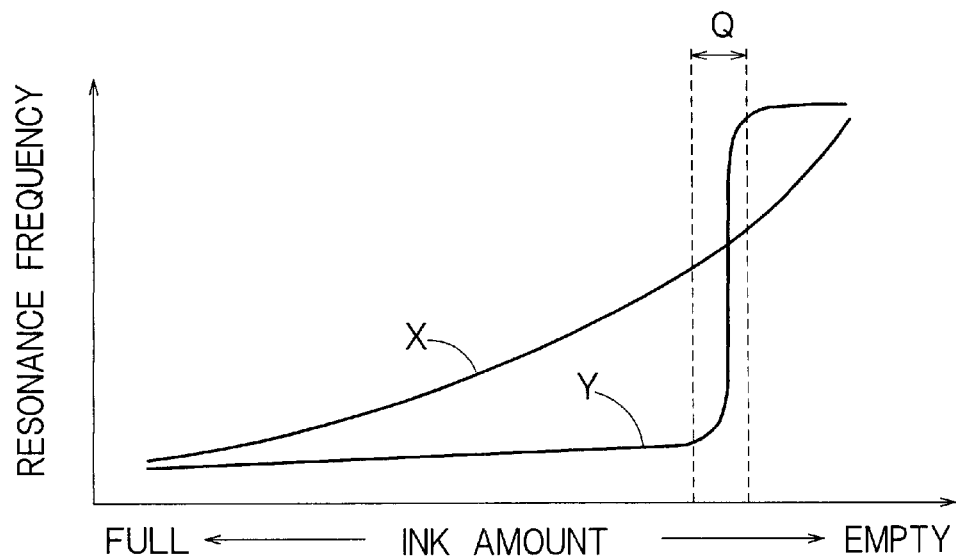
FIG. 3A is a graph showing the variation of resonance frequency of the ink measured by the actuator with the quantity of ink.

FIG. 3A is a graph showing the variation of the resonance frequency $f_s$ of the vibrating part with the quantity of the liquid contained in the ink container, in which resonance frequency $f_s$ is measured on the vertical axis and the quantity of the liquid contained in the ink container is measured on the horizontal axis. In the following description, the liquid is supposed to be an ink by way of example. The resonance frequency $f_s$ increases as the quantity of the residual ink decreases, when the composition of the ink remains constant.

The maximum additional inertance $M'_{max}$ of the vibrating part of the actuator 106 is expressed by Expression (4) when the space around the vibrating part of the actuator 106 is filled up with the ink. The transient inertance $M'_{var}$ in a state where the ink is consumed, some of the ink remains in the cavity 162 and the space around the vibrating part of the actuator 106 is not filled up with the ink is calculated by using Expression (6) on the basis of the thickness t of the film of the ink. In Expression (6), the parameter t is the thickness of the ink affecting the vibration of the vibrating part. Therefore, the process of gradual consumption of the ink can be detected (FIG. 2, (C)) when the thickness d of the cavity 162 of the actuator 106 (FIG. 1B) is small and the substrate 178 is sufficiently thin. The thickness $t_{ink}$ of the film of the ink affecting the vibration is equal to $t_{ink-max}$ when the additional inertance is equal to the maximum additional inertance $M'_{max}$.

Suppose, for example, that the actuator 106 is attached to the bottom wall of an ink container with the diaphragm 176 extended in substantially parallel to the level of the ink contained in the ink cartridge. After the level of the ink has dropped below a level at a height equal to the thickness $t_{ink-max}$ from the surface of the diaphragm 176 facing the cavity 162 with the consumption of the ink, transient additional inertance $M'_{var}$ (Expression (6)) changes gradually and the resonance frequency $f_s$ changes (Expression (1)) accordingly. The actuator 106 is able to detect the gradual consumption of the ink while the level of the ink is within the range of the thickness t.

Suppose, for example, that the actuator 106 is attached to a side wall of an ink cartridge with the diaphragm 176 extended substantially perpendicularly to the level of the ink contained in the ink cartridge. After the level of the ink has dropped to a level corresponding to the vibrating part of the actuator 106 with the consumption of the ink, the additional inertance M' decreases as the level of the ink drops and, consequently, the resonance frequency $f_s$ increases gradually (Expression (1)). Therefore, the actuator 106 is able to detect the gradual consumption of the ink while the level of the ink is in the range of the diameter 2a of the cavity 162 (FIG. 2, (C)).

In FIG. 3A, a curve X indicates variation of the resonance frequency f of the vibrating part with the quantity of the ink contained in the ink cartridge when the depth of the cavity 162 of the actuator 106 as attached to the bottom wall of the ink cartridge is sufficiently small or the vibrating part of the actuator 106 as attached to the side wall of the ink cartridge is sufficiently large of long. It is known from FIG. 3A that the resonance frequency $f_s$ of the ink and the vibrating part changes gradually as the quantity of the ink contained in the ink cartridge decreases.

More concretely, the gradual consumption of the ink can be detected in a state where both a liquid and air respectively having different densities exist around the vibrating part of the actuator 106 and affect the vibration of the vibrating part. As the ink is consumed gradually, the liquid decreases and air increases in the space around the vibrating part of the actuator 106.

When the actuator 106 is disposed with the diaphragm 176 extended in parallel to the level of the ink and the thickness $t_{ink}$ is smaller than the thickness $t_{ink\text{-}max}$, both the ink and air affect the vibration of the actuator 106. Therefore:

$$M' = M'_{air} + M'_{ink} = \rho_{air} \cdot t_{air}/S + \rho_{ink} \cdot t_{ink}/S \qquad (8)$$

where $M'_{air}$ is the inertance of air, $M'_{ink}$ is the inertance of the ink, $\rho_{air}$ is the density of air, $\rho_{ink}$ is the density of the ink, $t_{air}$ is the thickness of a film of air affecting the vibration and $t_{ink}$ is the thickness of a film of the ink affecting the vibration.

As the ink decreases and air increases in the space around the vibrating part of the actuator 106, the thickness $t_{air}$ increases and the thickness $t_{ink}$ decreases when the actuator 106 is disposed with the diaphragm 176 extended substantially in parallel to the level of the ink. Consequently, the inertance $M'_{var}$ decreases gradually and the resonance frequency increases gradually. Thus the quantity of the ink remaining in the ink cartridge or the consumption of the ink can be determined. Expression (7) includes only the density of the ink as a parameter because Expression (7) is formed on an assumption that the density of air is negligibly small as compared with that of the liquid.

When the actuator 106 is disposed with the diaphragm 176 extended substantially perpendicularly to the level of the ink, it is considered that the vibrating part of the actuator 106 is considered to be a parallel circuit of an equivalent circuit, not shown, of a section in contact with the ink of the vibrating part, and an equivalent circuit, not shown, of a section in contact with air of the vibrating part. Then, $$1/M' = 1/M'_{air} + 1/M'_{ink} = S_{air}/(\rho_{air} \cdot t_{air}) + S_{ink}/(\rho_{ink} \cdot t_{ink}) \qquad (9)$$

where $S_{ink}$ is the area of the section in contact with the ink of the vibrating part of the vibrating part, and $S_{air}$ is the area of the section in contact with air of the vibrating part of the actuator 106.

Expression (9) is applied to expressing a state where the ink cannot be held in the cavity 162 of the actuator 106. Inertance in a state where the ink can be held in the cavity 162 of the actuator 106 is the sum of M' expressed by Expression (9) and $M'_{cav}$ expressed by Expression (7).

The resonance frequency of the vibration of the actuator 106 varies as the depth of the ink changes from a depth corresponding to $t_{ink\text{-}max}$ to a depth corresponding to d. Therefore the actuator 106 is unable to detect the gradual reduction of the ink in a state where the depth of the residual ink is slightly smaller than $t_{ink\text{-}max}$ and the actuator 106 is disposed with the diaphragm 176 extended in parallel to the level of the ink. A change of the quantity of the ink is determined on the basis of a change of the resonance frequency of the vibration of the actuator 106 resulting from a change of the quantity of the ink while the depth changes slightly from $t_{ink\text{-}max}$ to d. When the actuator 106 is attached to the side wall of the ink container and the cavity 162 has a small diameter, the resonance frequency of the vibration of the actuator 106 changes slightly while the level of the ink drops across the cavity 162. Therefore it is difficult to detect the gradual consumption of the ink while the level of the ink drops across the cavity 162 and hence it is possible to detect either the level of the ink above the upper end of the cavity 162 or that of the ink below the lower end of the cavity 162.

For example, a curve Y in FIG. 3A indicates variation of the resonance frequency $f_s$ of the vibrating part with the quantity of the ink contained in the ink cartridge when the vibrating part of the actuator 106 has a circular shape of a small diameter. It is known from the curve Y that the resonance frequency $f_s$ changes sharply for a reduction Q of the quantity of the ink while the level of the ink contained in the ink container drops across the cavity 162. Thus, it is possible to determine whether or not a predetermined quantity of the ink remains in the ink container in a two-value detection mode.

A method of detecting the ink by using the actuator 106 brings the diaphragm 176 into direct contact with the ink and hence the accuracy of detection of the method using the actuator 106 is higher than that of determining the consumption of the ink through calculation using software. Whereas a method of detecting the ink through the detection of conduction between electrodes is affected by the position of the electrodes on the ink container and the type of the ink, a method of detecting the ink by using the actuator 106 is scarcely affected by the position of the actuator 106 on the ink container and the type of the ink.

Since the method using the actuator 106 is able to perform both oscillation and liquid detection, the number of sensors needed by the method using the actuator 106 and to be attached to the ink container is less than that of sensors needed by a method that uses different sensors for detecting oscillation and the ink. Thus an ink container capable of measuring the quantity of the ink remaining therein can be manufactured at a low manufacturing cost. Preferably, the frequency of vibration of the piezoelectric layer 160 is outside an audio frequency range to reduce noise generated by the actuator 106.

Figure 3B:
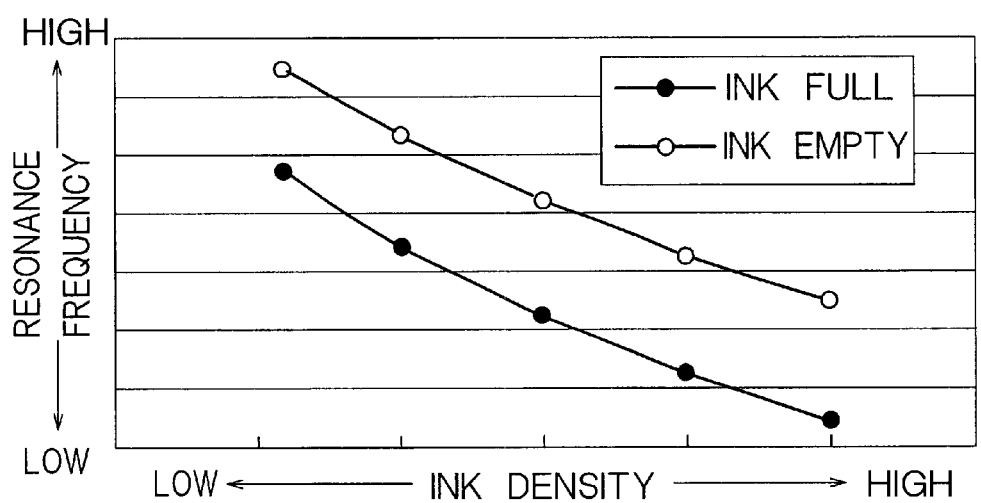
FIG. 3B is a graph showing the variation of resonance frequency of ink with the density of the ink.

FIG. 3B shows the dependence of the resonance frequency $f_s$ of the vibrating part and the density of the ink by way of example. In the following description, the liquid is supposed to be an ink. In FIG. 3B, "Full" and "Empty" signify two different relative states and do not signify a state where the ink container is actually fully filled with the ink and a state where the ink container is actually completely empty. As obvious from FIG. 3B, the resonance frequency $f_s$ decreases with the increase of the density of the ink because the additional inertance increases as the density of the ink increases; that is, the resonance frequency $f_s$ is dependent on the type of the ink. Thus, it is possible, when refilling the ink container with the ink, to decide whether or not a wrong ink of a density different from that of the correct ink is filled in the ink container. Accordingly, ink containers respectively containing different types of inks can be discriminated from each other.

Description will be given of conditions for enabling accurate detection of the condition of the liquid contained in the ink container, when the size and shape of the cavity 162 of the actuator 106 are determined such that the liquid remains in the cavity 162 in a state where the ink container is empty. The actuator 106 capable of detecting the condition of the liquid in a state where the cavity 162 is filled up with the liquid is capable of detecting the condition of the liquid also in a state where the cavity 162 is not filled up with the liquid.

Resonance frequency $f_s$ is a function of inertance M, and inertance M is the sum of the inertance $M_{act}$ of the vibrating part and additional inertance M'. Additional inertance M' is dependent on the condition of the liquid. Additional inertance M' is a value indicating an apparent increase in the mass of the vibrating part by the liquid existing in the vicinity of the vibrating part; that is, additional inertance M' is an apparent increment of the mass of the vibrating part caused by the liquid.

Therefore, if $M'_{cav}$ is greater than $M'_{max}$ expressed by Expression (4), the liquid that increases the apparent mass of the vibrating part is the liquid remaining in the cavity 162. This state is the same as a state where the ink container is filled up with the liquid. The additional inertance of the liquid affecting the vibration of the vibrating part does not decrease below $M'_{max}$ in this state and hence the consumption of the liquid cannot be measured.

If $M'_{cav}$ is smaller than $M'_{max}$ expressed by Expression (4), the liquid remaining in the cavity 162, and air contained in the ink container or a vacuum space increase the apparent mass of the vibrating part. This state, differing from the state where the ink container is filled up with the liquid, causes additional inertance M' to change and hence the resonance frequency $f_s$ changes. Therefore, the actuator 106 is able to detect the condition of the liquid in the ink container.

Thus $M'_{cav}$ must be smaller than $M'_{max}$ to enable the actuator 106 to detect the condition of the liquid accurately in a state where the ink container is empty and the liquid remains in the cavity 162 of the actuator 106. The condition, $M'_{max} > M'_{cav}$ for enabling the actuator 106 to detect the condition of the liquid accurately is not dependent on the shape of the cavity 162.

The additional inertance $M'_{cav}$ is equivalent to the mass of a volume of the liquid substantially equal to that of the cavity 162. Therefore, as obvious from the inequality: $M'_{max} > M'_{cav}$ the condition for enabling the actuator 106 to detect the condition of the liquid accurately can be expressed by a condition specifying the volume of the cavity 162. Suppose that the cavity 162 has the shape of a circular cylinder, the opening 161 has a radius a and the cavity has a depth d. Then, $$M'_{max} > \rho \cdot d/\pi a^2 \tag{10}$$

Developing Expression (10), we obtain $$a/d > 3\pi/8 \tag{11}$$

Thus, if the radius a of the opening 161 of the actuator 106 and the depth d of the cavity 162 of the actuator 106 satisfy Expression (11), the actuator 106 is able to detect the condition of the liquid correctly even in a state where the ink container is empty and the liquid remains in the cavity 162.

Expressions (10) and (11) apply only to a case where the cavity 162 has the shape of a circular cylinder. When the cavity 162 is not cylindrical, the term, $\pi a^2$ of Expression (10) is replaced with a term representing the area of the cavity 162 for calculation to determine the relation between the dimensions, i.e., the width and length, of the cavity 162 and the depth of the cavity 162.

Since the additional inertance M' affect acoustic impedance, it is considered that the method of measuring the back electromotive force generated by the residual vibration of the actuator 106 measures at least the variation of acoustic impedance.

Figure 4A:
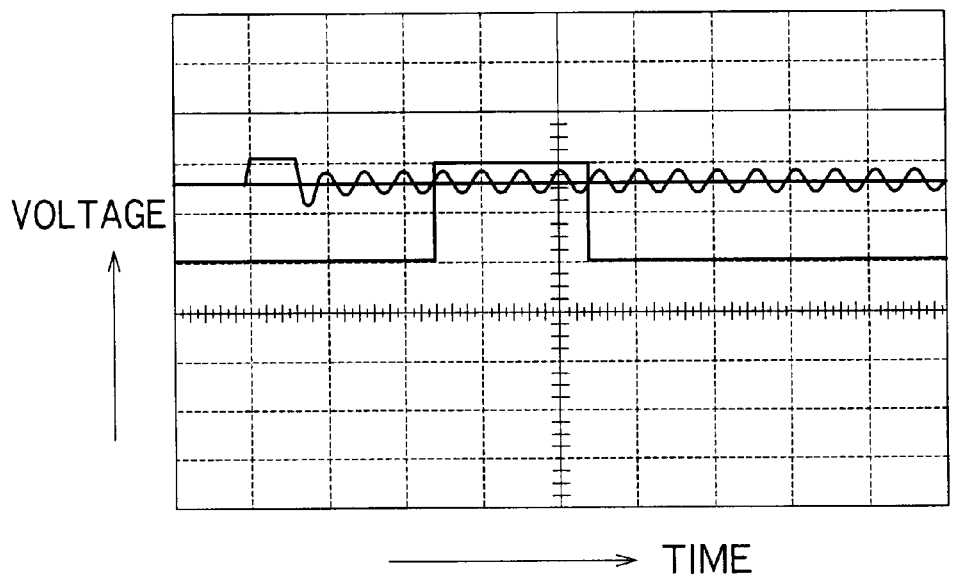
FIGS. 4A and 4B are graphs showing the waveforms of back electromotive force generated by the actuator shown in FIGS. 1A, 1B and 1C.
Figure 4B:
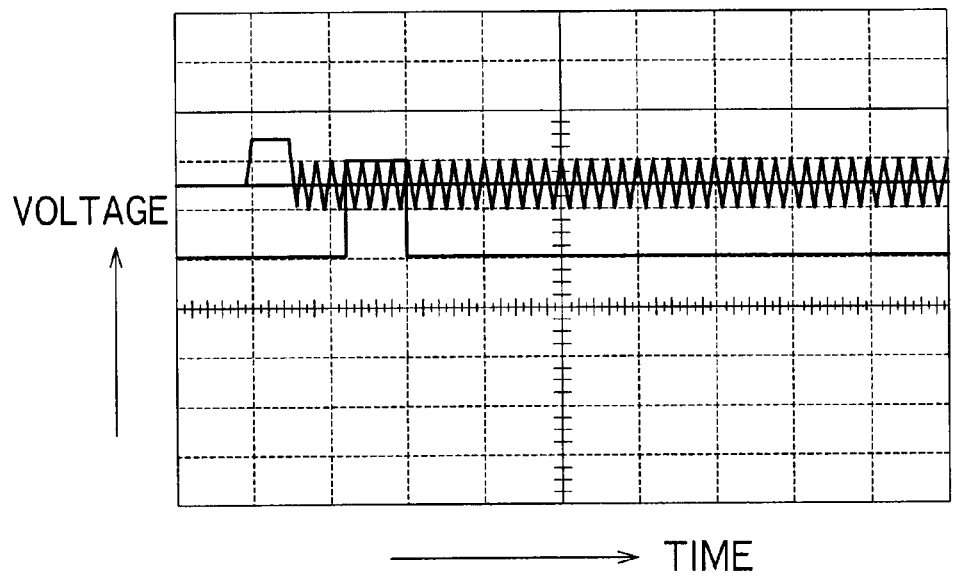

FIGS. 4A and 4B are graphs of assistance in explaining a residual vibration measuring method, showing the waveforms of voltage signals representing back electromotive force generated by the residual vibration of the actuator 106 after the vibrating part of the actuator 106 has been driven for vibration by a driving signal. The change of the level of the liquid relative to a level corresponding to the position of the actuator 106 attached to the ink container can be detected through the detection of the change of the frequency or amplitude of residual vibration after the oscillation of the actuator 106. In FIGS. 4A and 4B, the voltage of back electromotive force generated by the residual vibration of the actuator 106 is measured on the vertical axis, and time is measured on the horizontal axis. Analog voltage signals of waveforms as shown in FIGS. 4A and 4B are generated by the residual vibration of the actuator 106. The analog voltage signal is converted into a digital value (binary value) corresponding to the frequency of the analog voltage signal. In the examples shown in FIGS. 4A and 4B, a time period corresponding to four successive pulses between the fourth and the eighth pulse is measured.

More specifically, the number of times of change of the voltage signal from a voltage on the lower side of a reference line indicating a predetermined reference voltage across the reference line to a voltage on the higher side of the reference line is counted after the oscillation of the actuator 106. A digital signal having a HIGH section corresponding to a section between the fourth change and the eighth change of the voltage signal is produced, and a time period from the fourth change and the eighth change is measured by using a predetermined clock signal.

FIG. 4A shows the waveform of a voltage signal generated when the level of the liquid is above the level corresponding to the position of the actuator 106, and FIG. 4B shows the waveform of a voltage signal generated when the liquid does not exist at the level corresponding to the position of the actuator 106. It is known from the comparative observation of FIGS. 4A and 4B that the time period from the fourth change (fourth count) to the eighth change (eighth count) in the voltage signal shown in FIG. 4A is longer than that in the voltage signal shown in FIG. 4B; that is, the time period between the fourth and the eighth change is dependent on the level of the liquid relative to that corresponding to the position of the actuator 106. Thus the consumption of the liquid can be detected by using the difference between the time periods.

The counting of changes in the voltage signal is started from the fourth change to count changes after the vibration of the actuator has stabilized. A change to be counted first is not limited to the fourth change, counting of changes may be started from any optional change. In this embodiment, the fourth to the eighth change of the voltage signal are detected and a time period corresponding to the fourth to the eighth change is measured by using a predetermined clock signal. The resonance frequency can be determined on the basis of the thus measured time period. Changes from the fourth to the eighth change do not necessarily need to be counted; changes from the fourth to the n-th (n is an optional integer) change may be counted. Although FIGS. 4A and 4B show a method of measuring the time period corresponding to a section of the voltage signal between the fourth to the eighth change, a time period corresponding to a section of the voltage signal between any optional changes may be measured when a frequency measuring circuit requires it.

When the liquid has a stable quality and the amplitude of the voltage signal varies in a narrow range, the resonance frequency may be determined on the basis of a time period corresponding to changes between the fourth and the sixth change to accomplish the detection quickly. If the liquid has an unstable quality and the amplitude of the voltage signal varies in a wide range, a time period corresponding to changes between the fourth and the twelfth change may be used for the accurate detection of the residual vibration.

Figure 5:
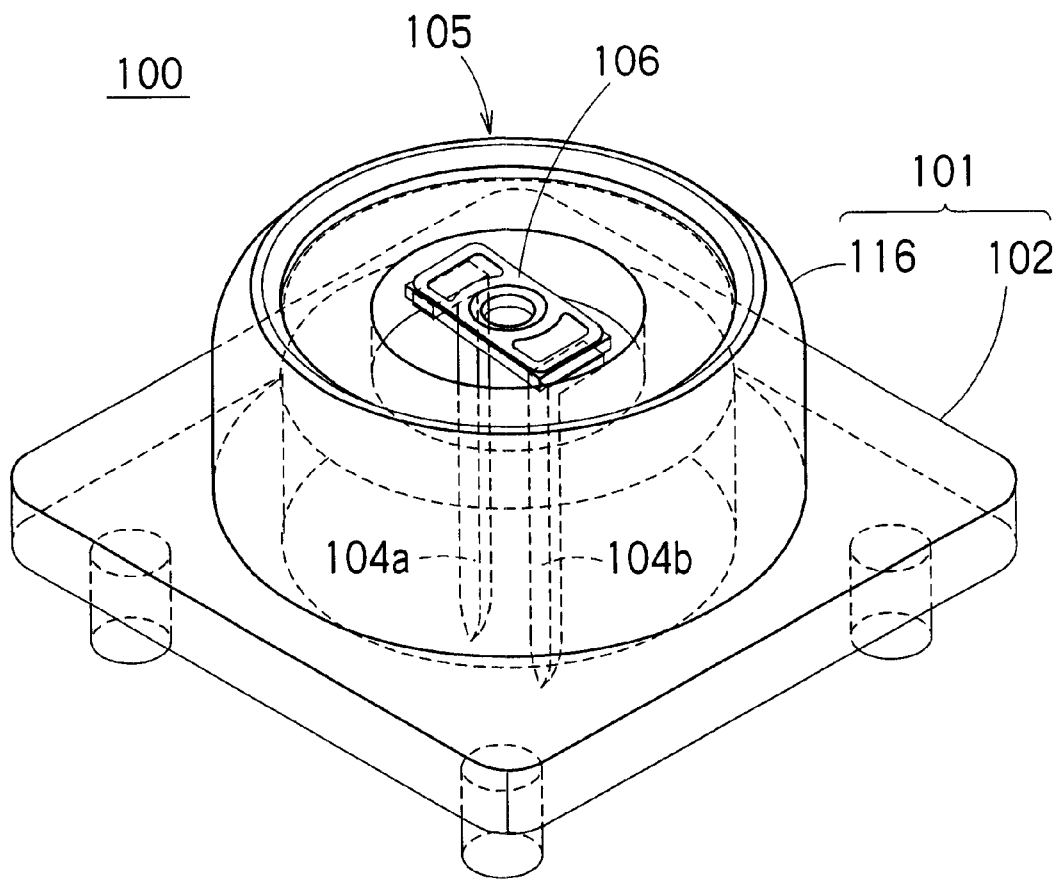
FIG. 5 is a perspective view of a monitoring module provided with the actuator shown in FIGS. 1A, 1B and 1C.
Figure 7:
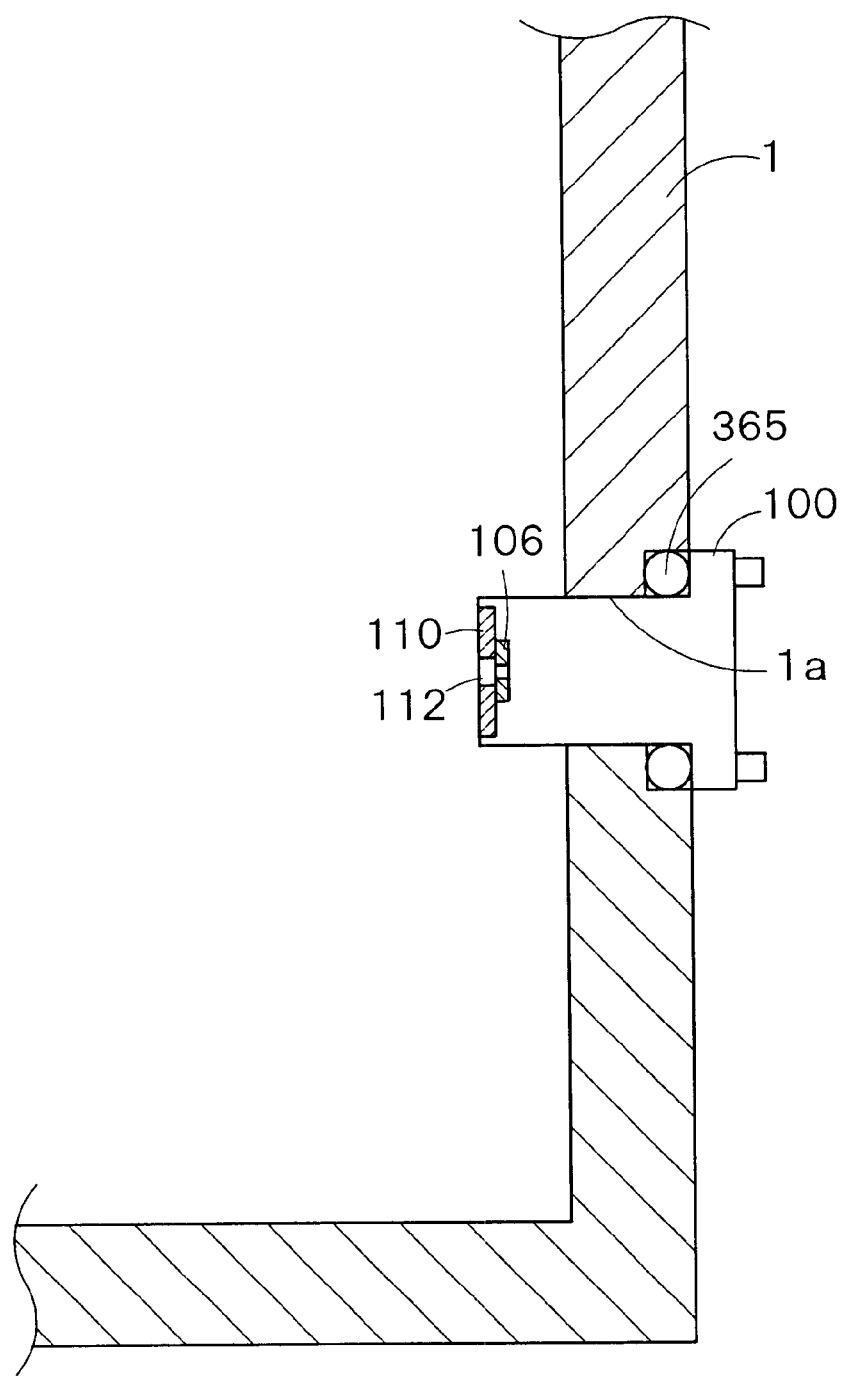
FIG. 7 is a fragmentary sectional view of an ink cartridge provided with the monitoring module shown in FIG. 5.

FIG. 5 is a perspective view of a monitoring module 100 including the actuator 106. The monitoring module 100 is attached to a predetermined part of an ink container 1 (as shown in FIG. 7), such as an ink cartridge. The monitoring module 100 determines a consumption of the liquid contained in the ink container 1 through the measurement of at least change in the acoustic impedance of the liquid contained in the ink container 1.

The monitoring module 100 has a connecting structure 101 for connecting the actuator 106 to the ink container 1. The connecting structure 101 includes a substantially rectangular base 102, and a cylindrical part 116 to house the actuator 106, which is driven for oscillation by a driving signal. The monitoring module 100 is formed such that nothing is able to reach the actuator 106 from outside when the monitoring module 100 is mounted on the ink container 1 to protect the actuator 106. The outer edge of the free end of the cylindrical part 116 is rounded to facilitate fitting the cylindrical part 116 in a hole formed in the ink container 1.

Figure 6:
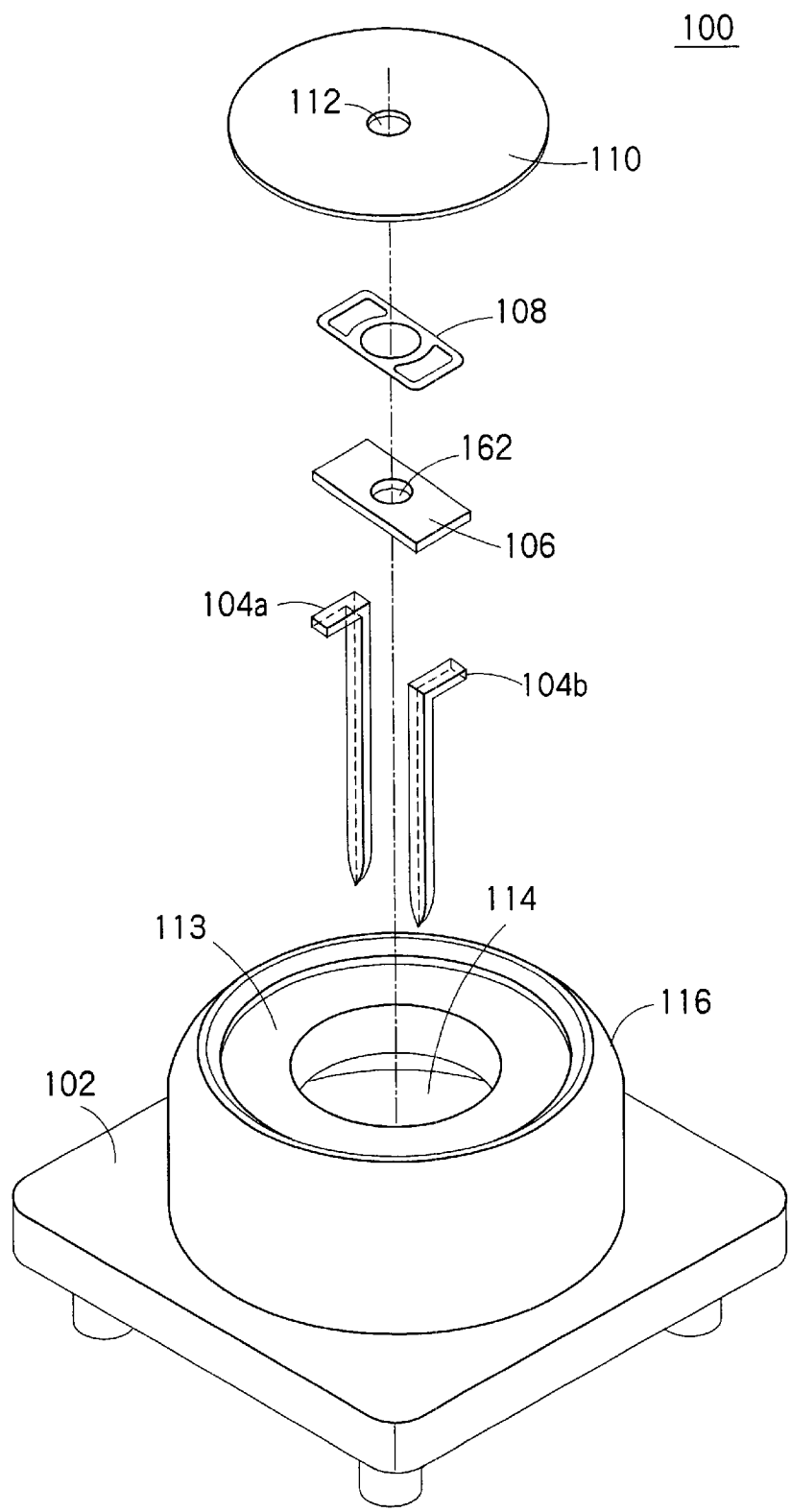
FIG. 6 is an exploded perspective view of the monitoring module shown in FIG. 5.

FIG. 6 is an exploded perspective view of the monitoring module 100 shown in FIG. 5. The monitoring module 100 includes the connecting structure 101 of a resin, a plate 110, an actuator holding part 105 (FIG. 5), leads 104a and 104b, the actuator 106, and a film 108. Preferably, the plate 110 is formed of a corrosion-resistant material, such as a stainless steel.

The leads 104a and 104b are extended in a cylindrical opening 114 extending through central parts of the base 102 and the cylindrical part 116 of the connecting structure 101. The actuator 106, the film 108 and the plate 110 are placed in a recess 113 formed contiguously with an end of the cylindrical opening 114.

The actuator 106 is bonded to the plate 110 by the film 108. The plate 110 and the actuator 106 are fixed to the bottom surface of the recess 113 of the connecting structure 101. Thus the leads 104a and 104b, the actuator 106, the film 108 and the plate 110 are incorporated into the connecting structure 101.

The leads 104a and 104b are connected to the upper electrode 164 and the lower electrode 166 of the actuator 106, respectively, to transmit a driving signal to the piezoelectric layer 160, and to transmit a resonance frequency signal representing a resonance frequency measured by the actuator 106 to a recording apparatus or the like.

The actuator 106 is driven by the driving signal applied thereto through the leads 104a and 104b for temporary oscillation. The residual vibration of the actuator 106 following the temporary oscillation generates back electromotive force. A resonance frequency corresponding to the condition of the liquid contained in the ink container can be determined through the measurement of the period of oscillation of a voltage signal representing the back electromotive force.

The film 108 bonds the actuator 106 to the plate 110 in a liquid-tight fashion. Preferably, the film 108 is formed of a polyolefin resin or the like and is bonded to the plate 110 by thermal bonding. The actuator 106 can be flatly bonded to the plate 110 with the film 108 at a correct position on the plate 110, so that parts other than the vibrating part do not vibrate. Thus the vibration characteristic of the actuator 106 does not change when the actuator 106 is bonded to the plate 110.

The plate 110 is circular, the opening 114 is cylindrical, and the actuator 106 and the film 108 are rectangular. The leads 104a and 104b, the actuator 106, the film 108 and the plate 110 may be detachable from the base 102. The base 102, the leads 104a and 104b, the actuator 106, the film 108 and the plate 110 are symmetrical with respect to the center axis of the monitoring module 100. The base 102, the actuator 106, the film 108 and the plate 110 are aligned substantially with the center axis of the monitoring module 100.

The opening 114 has a sectional area greater than the area of the vibrating part of the actuator 106. An opening 112 is formed in a central part of the plate 110 in alignment with the vibrating part of the actuator 106. As shown in FIGS. 1 and 2, the actuator 106 has a cavity 162. The opening 112 and the cavity 162 form an ink storage space. Preferably, the thickness of the plate 110 is smaller than the diameter of the opening 112 in view of reducing the effect of residual ink. For example, it is preferable that the depth of the opening 112 is ⅓ of the diameter of the same or below. The opening 112 is a substantially complete round having a center axis aligned with the center axis of the monitoring module 100. The area of the opening 112 is greater than the area of the open end of the cavity 162 of the actuator 106. The opening 112 may be tapered or stepped.

The monitoring module 100 is attached to a side wall, the top wall or the bottom wall of the ink container 1 so that the opening 112 opens into the interior of the ink container 1. When the liquid contained in the ink container is consumed and the liquid disappears from a space around the actuator 106, the resonance frequency of the actuator 106 changes greatly, and thereby the change of the level of the liquid can be detected.

FIG. 7 is a sectional view of a side wall of the ink container 1 and the monitoring module 100 fitted in an opening formed in the side wall. An O-ring 365 is held between the side wall of the ink container 1 and the monitoring module 100 to seal the gap between the monitoring module 100 and the ink container 1 in a liquid-tight fashion. It is preferable that the monitoring module 100 has the cylindrical part 116 (FIG. 5) to use the O-ring for sealing.

Thus an end part of the monitoring module 100 projects into the ink container 1 and the liquid contained in the ink container 1 flows through the opening 112 of the plate 110 into the cavity 162 of the actuator 106 to wet the vibrating part of the actuator 106. The resonance frequency of the residual vibration of the actuator 106 when the vibrating part of the actuator 106 is exposed to the liquid and that of the same when the vibrating part is exposed to air are different. Therefore the condition of consumption of the liquid can be detected through the measurement of the resonance frequency of the residual vibration of the actuator 106 by the monitoring module 100.

Figure 8:
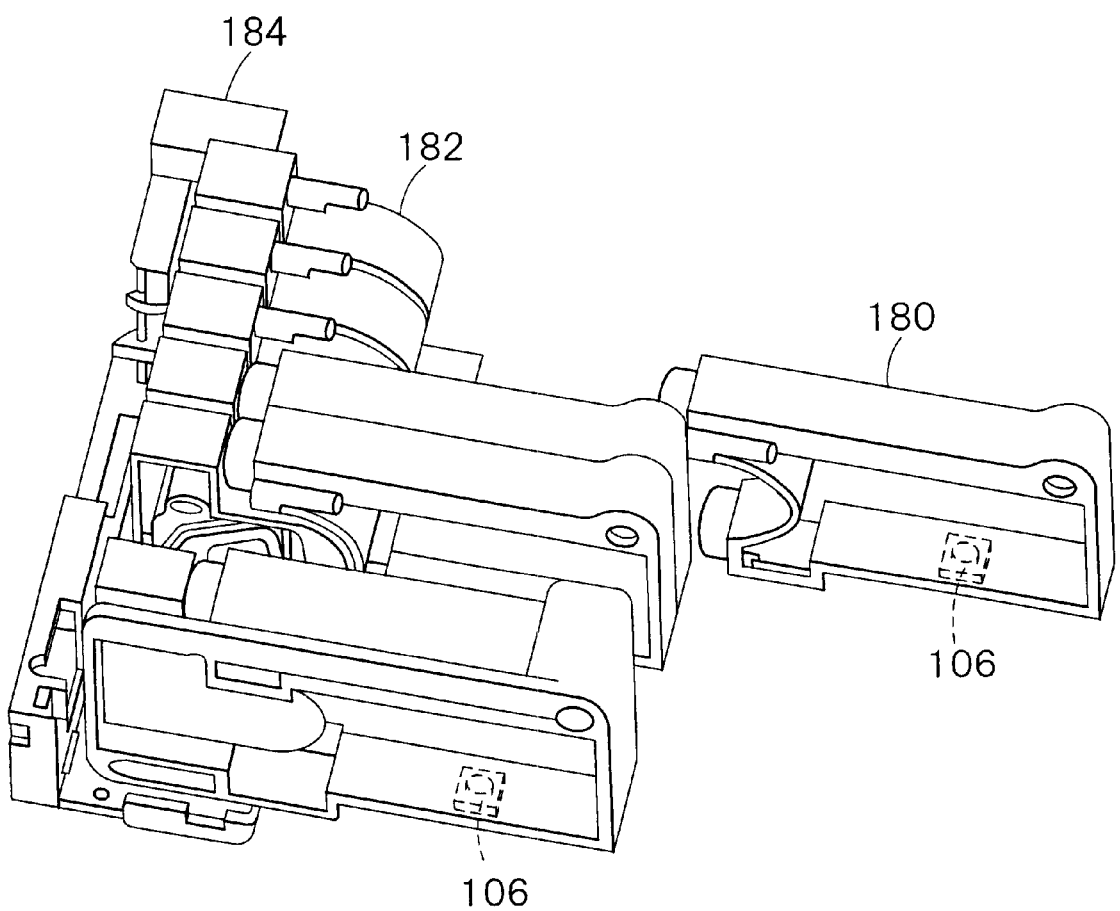
FIG. 8 is a perspective view of an ink-jet recording apparatus provided with ink cartridges each provided with the actuator shown in FIGS. 1A, 1B and 1C.

FIG. 8 is a perspective view of an ink-jet recording apparatus provided with ink cartridges 180 each provided with the actuator 106 shown in FIGS. 1A, 1B and 1C. The ink cartridges 180 are mounted on the ink-jet recording apparatus provided with a plurality of ink feed units 182 respectively corresponding to the plurality of ink cartridges 180, and a holder 184 holding the ink feed units 182. The ink cartridges 180 contain inks of different qualities, such as inks of different colors, respectively. Each of the ink cartridges 180 is provided on its bottom wall with the actuator 106 capable of detecting at least acoustic impedance. The quantity of the ink remaining in the ink cartridge 180 can be measured by the actuator 106 attached to the ink cartridge 180.

Figure 9:
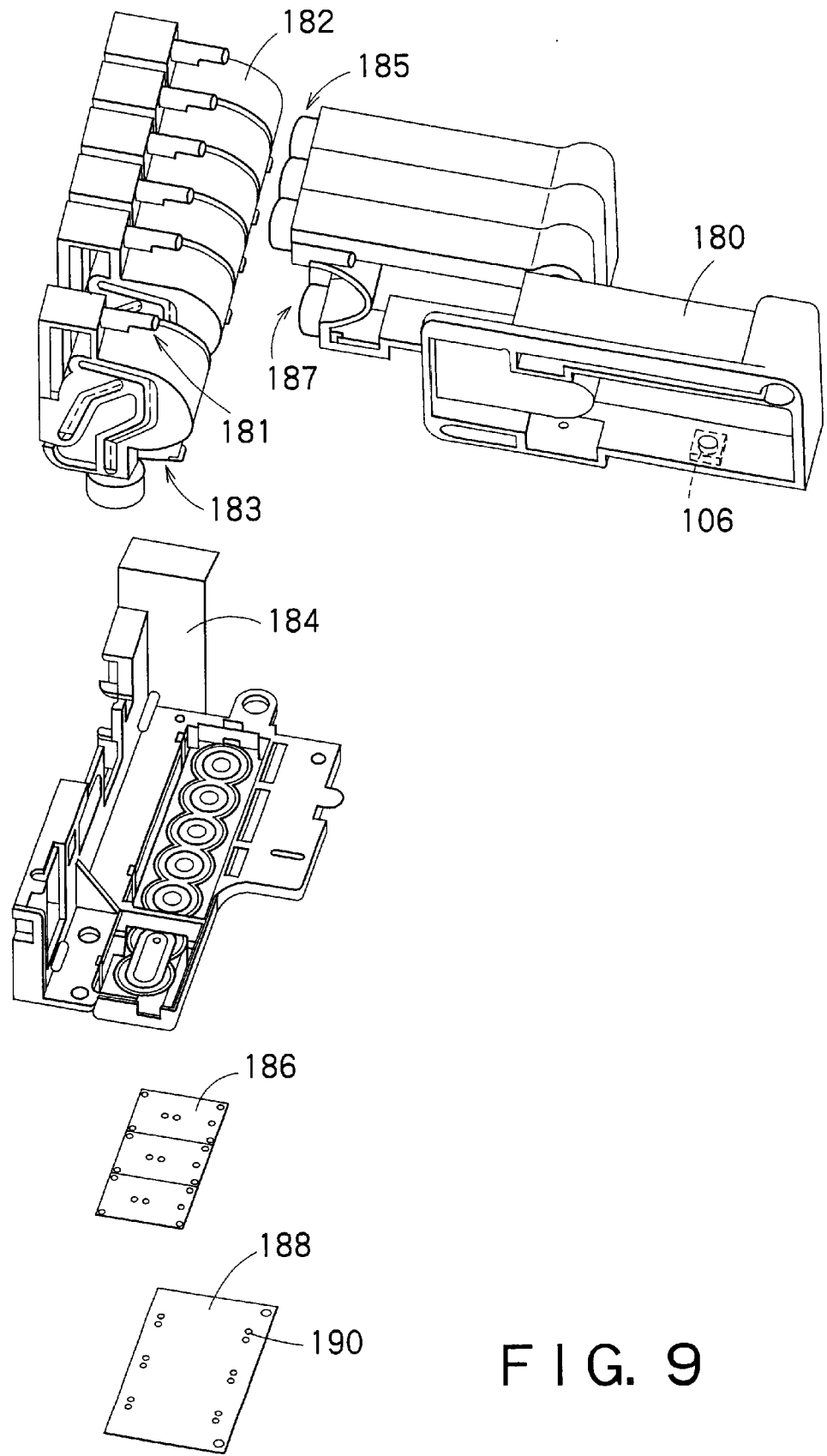
FIG. 9 is an exploded perspective view of an ink-jet recording apparatus provided with the actuator shown in FIGS. 1 and 2.

FIG. 9 is an exploded perspective view of the ink-jet recording apparatus, showing a recording head and peripheral components. The ink-jet recording apparatus has the ink feed units 182, the holder 184, a head plate 186, and a nozzle plate 188 provided with a plurality of ink-jetting nozzles 190.

Each of the ink feed units 182 has an air outlet 181 and an ink inlet 183. Air flows through the air outlet 181 into the ink cartridge 180. The ink flows from the ink cartridge 180 through the ink inlet 183 into the ink feed unit 182.

Each ink cartridge 180 has an air inlet 185 and an ink outlet 187. Air flows through the air outlet 181 of the ink feed unit 182 and the air inlet 185 into the ink cartridge 180.

The ink flows from the ink cartridge 180 through the ink outlet 187 and the ink inlet 183 of the ink feed unit 182 into the ink feed unit 182. Air flows through the air inlet 185 into the ink cartridge 180 to promote the flow of the ink from the ink cartridge 180 into the ink feed unit 182. The holder 184 guides the ink supplied from the ink cartridge 180 into the ink feed unit 182 to the head plate 186.

Figure 10:
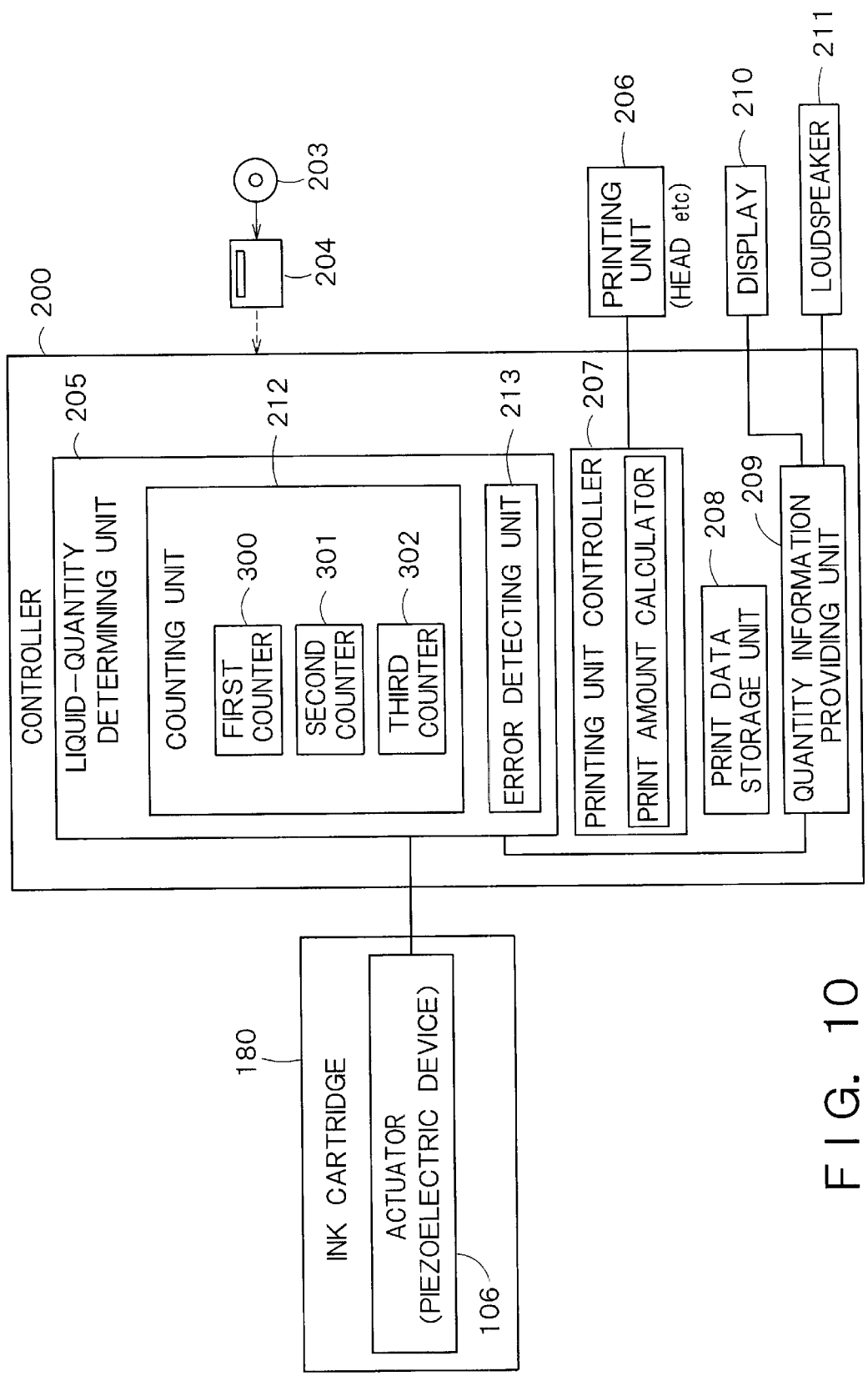
FIG. 10 is a block diagram of a principal part of an ink-jet recording apparatus in a preferred embodiment according to the present invention.

FIG. 10 is a block diagram of a principal part of the ink-jet recording apparatus of the present embodiment. Referring to FIG. 10, each ink cartridge 180 is provided with the actuator 106. At least a part of the vibrating part of the actuator 106 can be exposed to the interior space of the ink cartridge 180. The vibrating part of the actuator 106 is driven for vibration by the driving signal. The actuator 106 is capable of generating a voltage signal representing back electromotive force generated by the vibration of the vibrating part.

A controller 200 is a computer for controlling the ink-jet recording apparatus. The controller 200 may be either an internal device combined with the ink-jet recording apparatus or an external device, such as an external computer, connected to the ink-jet recording apparatus by communication lines. Programs specifying some of the functions of the controller 200 may be stored in a recording medium 203, such as a compact disk, and the recording medium 203 may be loaded to an input device 204, such as a CD drive.

The controller 200 has a liquid-quantity determining unit 205 for determining the quantity of the ink remaining in a space facing the vibrating part of the actuator 106. The liquid-quantity determining unit 205 determines the quantity of the ink remaining in the cartridge 180 by feeding a driving signal to the actuator 106 to drive the vibrating part for vibration, and measuring the resonance frequency of the residual vibration of the vibrating part following the vibration caused by the driving signal.

The liquid-quantity determining unit 205 includes a counting unit 212 capable of counting the pulses of a residual vibration signal generated by the residual vibration and of measuring a time period necessary for counting a predetermined number of pulses. The counting unit 212 is provided with three counters, i.e., a first counter 300, a second counter 301 and a third counter 302. The counters 300, 301 and 302 start counting the pulses at different starting time points, respectively. Thus, the pulses are counted three times.

The liquid-quantity determining unit 205 includes an error detecting device 213. The error detecting device 213 decides that the operation of the counting unit 212 for counting the pulses is defective when the differences between the measured time periods are greater than an allowable limit.

Preferably, the liquid-quantity determining unit 205 is capable of deciding whether or not the level of the ink has passed a level corresponding to the vibrating part of the actuator 106 by using a fact that the resonance frequency of the residual vibration signal in a state as shown in FIG. 2, (E), where the ink exists in the cavity 162 and does not exist in the space around the cavity 126 and that in a state as shown in FIG. 2, (C), where both the cavity 162 and the space around the cavity 162 are filled up with the ink are different.

The controller 200 further includes a printing unit controller 207 for controlling a printing unit 206, a print data storage unit 208, and a quantity information providing unit 209. The quantity information providing unit 209 gives quantity information about the quantity determined by the liquid-quantity determining unit 205 to a display 210 and a loudspeaker 211 to inform the user of the quantity of the ink. For example, the display 210 displays a diagram indicating the condition of consumption of the ink, and the loudspeaker radiates an information sound or a synthetic speech indicating the quantity of the residual ink. Proper guidance may be given by synthetic speeches.

Information about the condition of consumption of the ink may be provided in response to a request made by the user, may be periodically provided, or may be provided at the occurrence of a specific event, such as the start of the printing operation. The information about the condition of consumption of the ink may be automatically provided upon the reduction of the quantity of the residual ink below a predetermined threshold corresponding to the exhaustion of the ink.

Figure 11:
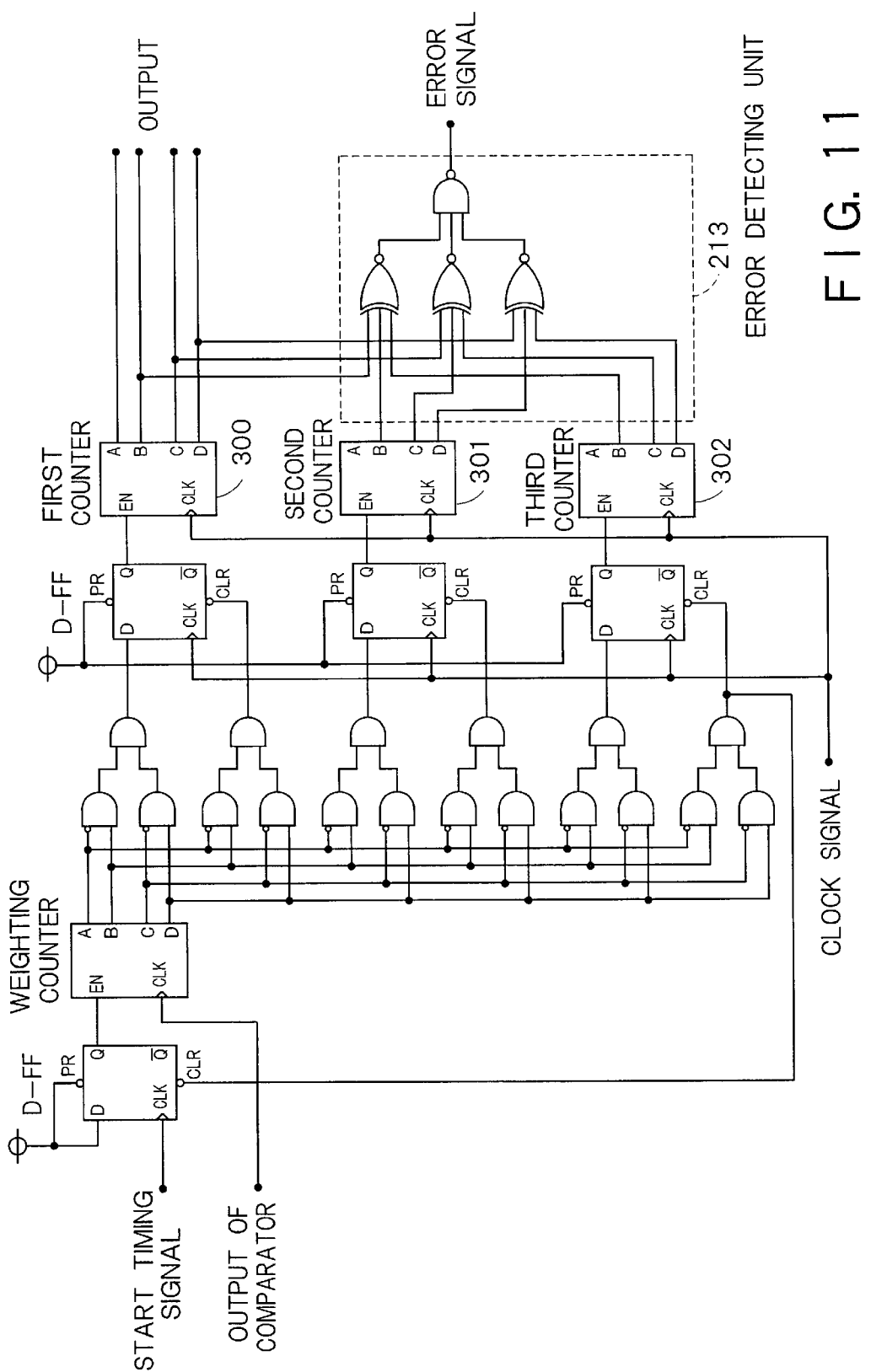
FIG. 11 is a circuit diagram of a liquid-quantity determining unit included in the liquid-quantity monitoring apparatus in a preferred embodiment according to the present invention.

FIG. 11 is a circuit diagram of the liquid-quantity determining unit 205. The liquid-quantity determining unit 205 includes the three counters 300, 301 and 302, and the error detecting device 213. The error detecting device 213 regards the least significant bit as a measuring error and ignores the same.

Figure 12:
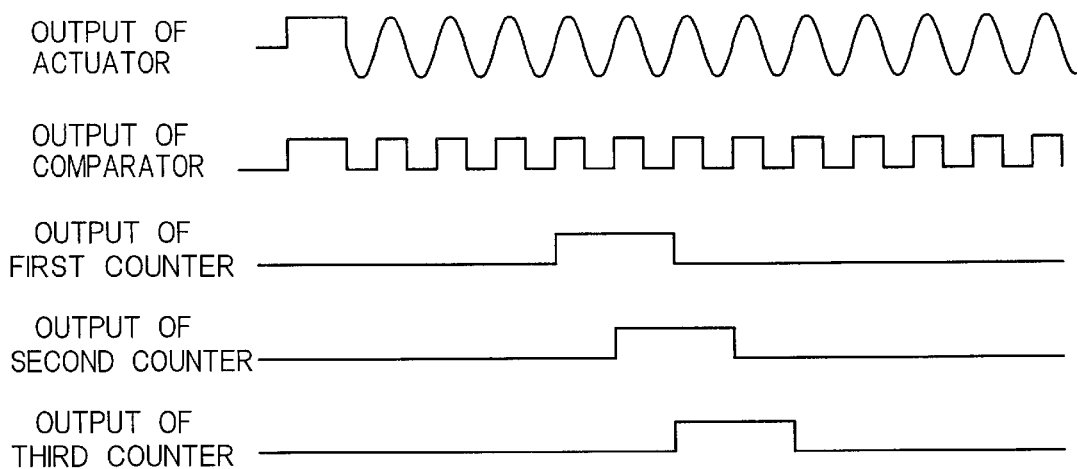
FIG. 12 is a waveform diagram of assistance in explaining the operation of the liquid-quantity monitoring apparatus in the preferred embodiment, showing the waveforms of signals provided when measurement is correct.
Figure 13:
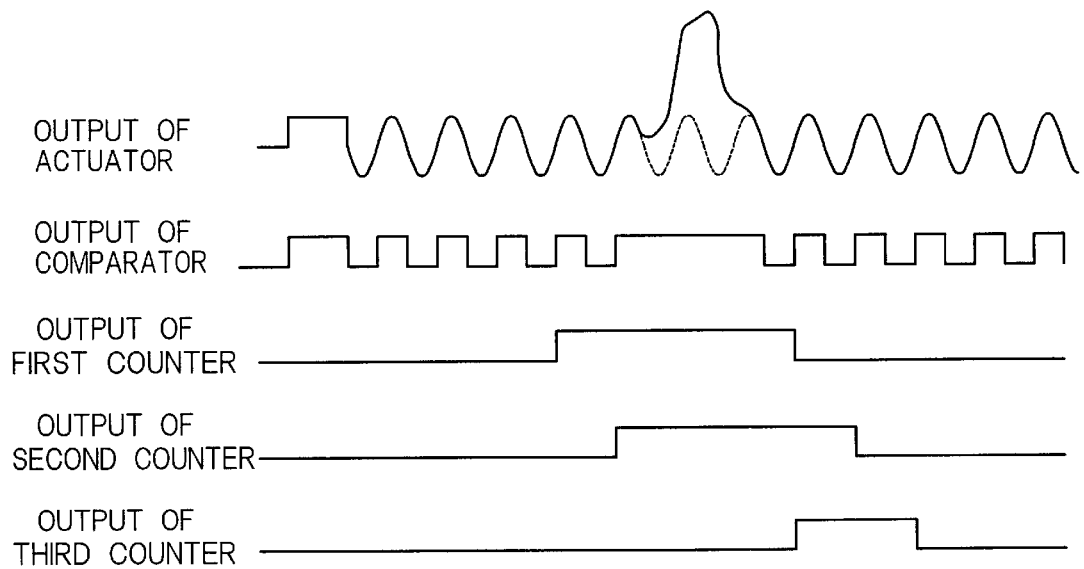
FIG. 13 is a waveform diagram of assistance in explaining the operation of the liquid-quantity monitoring apparatus in the preferred embodiment, showing the waveforms of signals provided when measurement is incorrect.

FIGS. 12 and 13 are waveform charts of assistance in explaining the operations of an liquid-quantity monitoring apparatus according to the present embodiment including the actuator 106 and the liquid-quantity determining unit 205. FIG. 12 shows signals provided when the liquid-quantity determining unit 205 determines the quantity of the ink correctly, and FIG. 13 show signals provided when the liquid-quantity determining unit 205 determines the quantity of the ink incorrectly. In FIG. 13, an actuator output signal provided by the actuator 106 includes noise.

As shown in FIGS. 12 and 13, first four successive pulses of an output signal of a comparator are ignored because the waveform of the output of the actuator 106 has not stabilized yet. The first counter 300 measures a time period corresponding to two pulses from the fifth pulse, the second counter 301 measures a time period corresponding to two pulses from the sixth pulse, and the third counter measures a time period corresponding to two pulses from the seventh pulse.

Thus the starting time points at which the three counters 300, 301 and 302 start counting pulses, respectively, are determined such that the time periods measured by the first counter 300 and the third counter 302 do not overlap each other, and the time period measured by the second counter 301 overlap both the time periods measured respectively by the first counter 300 and the third counter 302.

As obvious from FIG. 12, when the liquid-quantity determining unit 205 determines the quantity of the ink correctly, the time periods measured respectively by the three counters 300, 301 and 302 are equal to each other. As obvious from FIG. 13, when the residual vibration signal provided by the actuator 106 includes noise, the time periods measured respectively by the three counters 300, 301 and 302 are different from each other.

Therefore, when the differences between the time periods measured by the counters 300, 301 and 302 are not greater than a predetermined allowable error limit, the measured result is reliable. On the other hand, when the differences between the time periods measured by the counters 300, 301 and 302 are greater than the predetermined allowable error limit, it is decided that the measurement is affected by noise.

Figure 14:
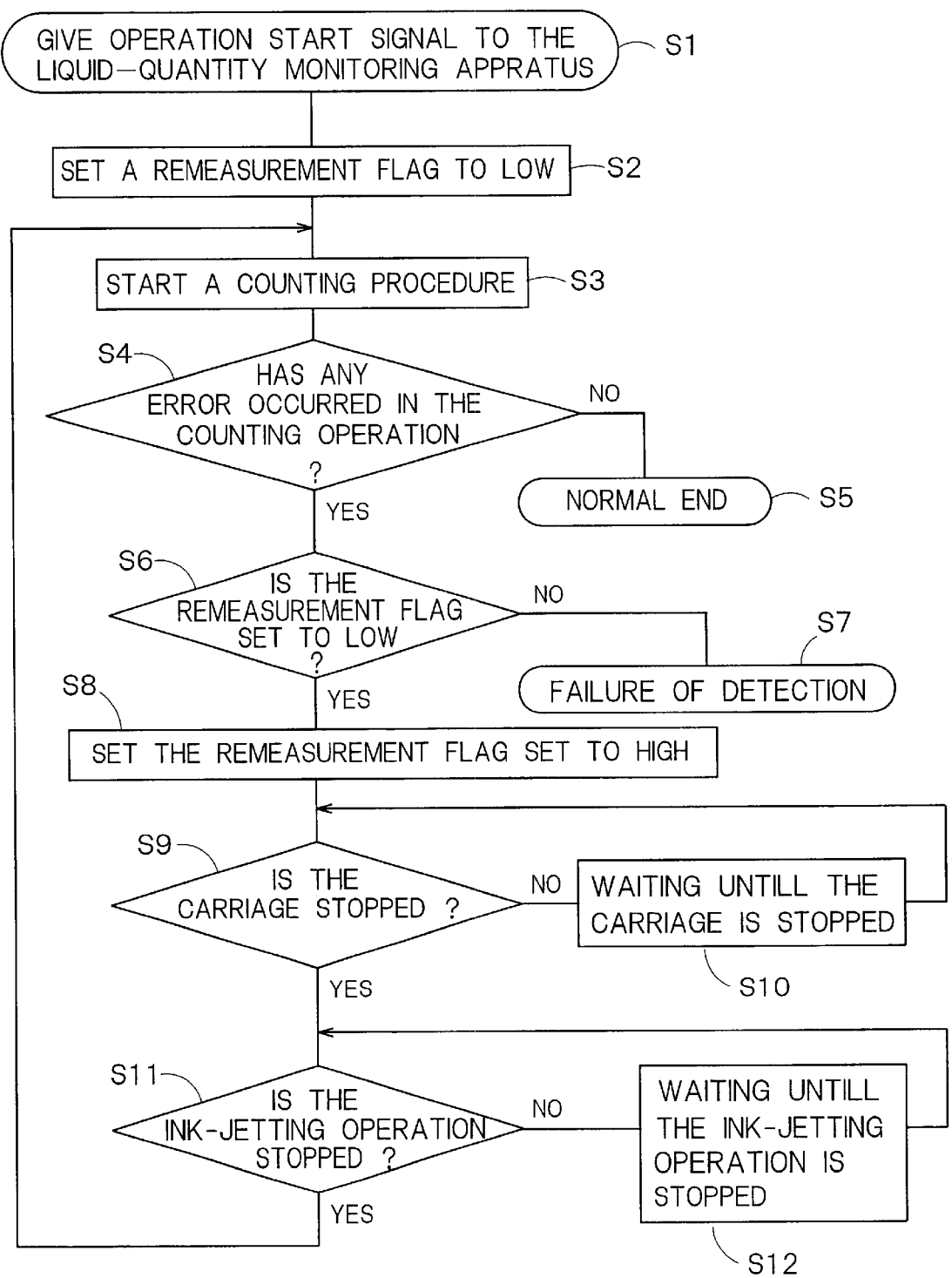
FIG. 14 is a flow chart of a liquid-quantity determining procedure to be carried out by the liquid-quantity determining unit of the liquid-quantity monitoring apparatus in the preferred embodiment.

FIG. 14 is a flow chart of a liquid-quantity determining procedure to be carried out by the liquid-quantity determining unit 205, and FIG. 15 is a flow chart of a counting procedure to be executed in step S3 of the liquid-quantity determining procedure shown in FIG. 14.

Referring to FIG. 14, an operation start signal is given to the liquid-quantity monitoring apparatus in step S1. Then, a remeasurement flag is set to LOW in step S2 and a counting procedure is started in step S3. A query is made in step S4 to see if any error occurred in the counting operation. If the response in step S4 is negative, the program goes to step S5 for normal end.

In the response in step S4 is affirmative, a query is made in step S6 to see if the remeasurement flag is set to LOW. If the response in step S7 is negative, it is decided that detection failed in step S7. If the response in step S6 is affirmative, the remeasurement flag is set to HIGH in step S8, and a query is made in step S9 to see if the carriage is stopped. If the carriage is not stopped, the program waits in step S10 until the carriage is stopped. If the carriage is stopped, a query is made in step S11 to see if the ink-jetting operation is stopped. If the ink-jetting operation is not stopped, the program waits in step S12 until the ink-jetting operation is stopped. If the ink-jetting operation is stopped, the program returns to step S3 to execute the counting procedure again.

In FIG. 15 showing the counting procedure, the character α indicates the number of pulses ignored before the first counter 300 starts counting, the character β indicates the number of pulses provided in a time period after the first counter 300 has started counting and before the second counter 301 starts counting, the character γ indicates the number of pulses provided in a time period after the first counter 300 has started counting and before the third counter 302 starts counting, and the character δ indicates the number of pulses to be counted by the counters 300, 301 and 302.

Referring to FIG. 15, the first counter 300 is queried in step S20 to see if the number of pulses has reached α. If the response in step S20 is affirmative, the first counter 300 starts counting pulses in step S21. A query is made in step S22 to see if the number of pulses has reached α+δ. If the response is affirmative, the first counter 300 is stopped in step S23.

The second counter 301 is queried in step S30 to see if the number of pulses has reached α+β. If the response is affirmative, the second counter 301 starts counting pulses in step S31. A query is made in step S32 to see if the number of pulses has reached α+β+δ. If the response is affirmative, the second counter 301 is stopped in step S33.

The third counter 302 is queried in step S40 to see if the number of pulses has reached α+γ. If the response is affirmative, the third counter 302 starts counting pulses in step S41. A query is made in step S42 to see if the number of pulses has reached α+γ+δ. If the response is affirmative, the third counter 302 is stopped in step S43.

After all the counters 300, 301 and 302 have been stopped, a query is made in step S50 to see if the respective high-order significant bits of signals provided by the counters 300, 301 and 302 coincide with each other. An error occurrence signal is generated in step S51 if the response is negative, or the counting procedure is ended if the response is affirmative.

As apparent from the foregoing description, according to the present invention, the liquid-quantity determining unit counts the pulses of the residual vibration signal generated by the actuator at least three times, measures the time periods each necessary for counting the predetermined number of pulses, and decides that the measurement is incorrect when the differences between the time periods are greater than the predetermined allowable limit. Thus the liquid-quantity monitoring apparatus is able to monitor the level of the liquid with reliability even in an environment where the output of the actuator is liable to include noise. The liquid-quantity monitoring apparatus is particularly effective in application to monitoring the quantity of the ink contained in an ink cartridge loaded into an ink-jet recording apparatus because the operation of the carriage mounted with the recording head and the ink-jetting operation are liable to introduce noise into the output signal of the actuator.

Although the invention has been described in its preferred embodiment with a certain degree of particularity, obviously many changes and variations are possible therein. It is therefore to be understood that the present invention may be practiced otherwise than as specifically described herein without departing from the scope and spirit thereof.

What is claimed is:

1. A liquid-quantity monitoring apparatus comprising:
   a piezoelectric device having a vibrating part capable of being exposed at least partly to a liquid-containing space for containing a liquid, the piezoelectric device being capable of vibrating the vibrating part by a given drive signal and of generating a signal representing back electromotive force generated by vibration of the vibrating part; and
   a liquid-quantity determining means for determining a quantity of the liquid remaining in the liquid-containing space, to which the vibrating part is exposed, based on a resonance frequency of a residual vibration signal which is output from the piezoelectric device due to a residual vibration of the vibrating part after the vibrating part has been vibrated by the drive signal;
   wherein the liquid-quantity determining means counts a number of pulses included in the residual vibration signal, measures a time period necessary for counting a predetermined number of pulses after starting counting the pulses, and determines the quantity of the liquid based on the time period which has been measured; and
   wherein the liquid-quantity determining means repeats a pulse-counting operation for counting the predetermined number of pulses with different starting time points, and decides that a measurement is incorrect when differences between the time periods measured by the pulse-counting operations are greater than a predetermined allowable limit.

2. The liquid-quantity monitoring apparatus according to claim 1, wherein the pulse-counting operation is repeated at least three times; and
   wherein the starting time points when the pulse-counting operation is to be started for first, second and third pulse-counting cycles are so determined that a time period necessary for counting the predetermined number of pulses in the first pulse-counting cycle and a time period necessary for counting the predetermined number of pulses in the third pulse-counting cycle do not overlap each other, and a time period necessary for counting the predetermined number of pulses in the second pulse-counting cycle overlaps the time periods necessary for counting the predetermined number of pulses in the first and the third pulse-counting cycles.

3. The liquid-quantity monitoring apparatus according to claim 1, wherein the liquid-quantity determining means measures again the time periods each necessary for counting the predetermined number of pulses when the measurement is judged to be incorrect.

4. The liquid-quantity monitoring apparatus according to claim 3, wherein the liquid is contained in an ink container for an ink-jet recording head, the piezoelectric device being combined with the ink container such that at least part of the vibrating part of the piezoelectric device is exposed to an ink chamber formed in the ink container; and wherein the liquid-quantity determining means measures again the time periods each necessary for counting the predetermined number of pulses while a carriage holding the ink-jet recording head is stopped, when the measurement is judged to be incorrect.

5. The liquid-quantity monitoring apparatus according to claim 4, wherein the liquid-quantity determining means measures again the time periods each necessary for counting the predetermined number of pulses while an ink jetting operation of the ink-jet recording head is stopped, when the measurement is judged to be incorrect.

6. The liquid-quantity monitoring apparatus according to claim 3, wherein the liquid is contained in an ink container for an ink-jet recording head, the piezoelectric device being combined with the ink container with at least a part of the vibrating part thereof exposed to an ink chamber formed in the ink container; and
wherein the liquid-quantity determining means measures again the time periods each necessary for counting the predetermined number of pulses while an ink jetting operation of the ink-jet recording head is stopped, when the measurement is judged to be incorrect.

7. The liquid-quantity monitoring apparatus according to claim 1, wherein the liquid-quantity determining means is capable of deciding whether or not a level of the liquid passed a position where the vibrating part is positioned, based on a change of a resonance frequency of the residual vibration signal that occurs when the level of the liquid passes the vibrating part.

8. A liquid consuming apparatus comprising:
the liquid-quantity monitoring apparatus according to claim 1;
a liquid container combined with the piezoelectric device of the liquid-quantity monitoring apparatus; and
a liquid consuming unit that consumes a liquid supplied from the liquid container.

9. A computer readable recording medium storing a program to be executed by a computer system including at least one computer to realize functions of the liquid-quantity determining means of the liquid-quantity monitoring apparatus according to claim 1.

10. A liquid-quantity monitoring method comprising:
vibrating a vibrating part of a piezoelectric device by a given drive signal and generating a signal representing back electromotive force generated by vibration of the vibrating part;
determining a quantity of liquid remaining in a liquid-containing space, to which the vibrating part is exposed, by using a liquid quantity determining device which is based on a resonance frequency of a residual vibration signal which is output from the piezoelectric device due to a residual vibration of the vibrating part after the vibrating part has been vibrated by the drive signal;
counting a number of pulses included in the residual vibration signal;
measuring a time period necessary for counting a predetermined number of pulses after starting counting the pulses;
determining the quantity of the liquid based on the time period which has been measured;
repeating a pulse-counting operation for counting the predetermined number of pulses with different starting time points; and
deciding that a measurement is incorrect when differences between the time periods measured by the pulse-counting operations are greater than a predetermined allowable limit.

11. The liquid-quantity monitoring method according to claim 10, further comprising repeating the pulse-counting operation at least three times,
wherein the starting time points when the pulse-counting operation is to be started for first, second and third pulse-counting cycles are so determined that a time period necessary for counting the predetermined number of pulses in the first pulse-counting cycle and a time period necessary for counting the predetermined number of pulses in the third pulse-counting cycle do not overlap each other, and a time period necessary for counting the predetermined number of pulses in the second pulse-counting cycle overlaps the time periods necessary for counting the predetermined number of pulses in the first and the third pulse-counting cycles.

12. The liquid-quantity monitoring method according to claim 10, further comprising again measuring the time periods each necessary for counting the predetermined number of pulses when the measurement is judged to be incorrect.

13. The liquid-quantity monitoring apparatus according to claim 10, further comprising again measuring the time periods each necessary for counting the predetermined number of pulses while an ink jetting operation of an ink-jet recording head is stopped, when the measurement is judged to be incorrect,
wherein the liquid is contained in an ink container for an ink jet recording head.

14. The liquid-quantity monitoring method according to claim 10, further comprising deciding whether or not a level of the liquid is passed a position where the vibrating part is positioned, based on a change of a resonance frequency of the residual vibration signal that occurs when the level of the liquid passes the vibrating unit.

15. A liquid-quantity monitoring apparatus comprising:
a piezoelectric device having a vibrating part capable of being exposed at least partly to a liquid-containing space for containing a liquid, the piezoelectric device being capable of vibrating the vibrating part by a given drive signal and of generating a signal representing back electromotive force generated by vibration of the vibrating part; and
a liquid-quantity determining device for determining a quantity of the liquid remaining in the liquid-containing space, to which the vibrating part is exposed, based on a resonance frequency of a residual vibration signal which is output from the piezoelectric device due to a residual vibration of the vibrating part after the vibrating part has been vibrated by the drive signal;
wherein the liquid-quantity determining device counts a number of pulses included in the residual vibration signal, measures a time period necessary for counting a predetermined number of pulses after starting counting the pulses, and determines the quantity of the liquid based on the time period which has been measured; and
wherein the liquid-quantity determining device repeats a pulse-counting operation for counting the predetermined number of pulses with different starting time points, and decides that a measurement is incorrect when differences between the time periods measured by the pulse-counting operations are greater than a predetermined allowable limit.

16. The liquid-quantity monitoring apparatus according to claim 15, wherein the pulse-counting operation is repeated at least three times; and wherein the starting time points when the pulse-counting operation is to be started for first, second and third pulse-counting cycles are so determined that a time period necessary for counting the predetermined number of pulses in the first pulse-counting cycle and a time period necessary for counting the predetermined number of pulses in the third pulse-counting cycle do not overlap each other, and a time period necessary for counting the predetermined number of pulses in the second pulse-counting cycle overlaps the time periods necessary for counting the predetermined number of pulses in the first and the third pulse-counting cycles.

17. The liquid-quantity monitoring apparatus according to claim 15, wherein the liquid-quantity determining device measures again the time periods each necessary for counting the predetermined number of pulses when the measurement is judged to be incorrect.

18. The liquid-quantity monitoring apparatus according to claim 17, wherein the liquid is contained in an ink container for an ink-jet recording head, the piezoelectric device being combined with the ink container such that at least part of the vibrating part of the piezoelectric device is exposed to an ink chamber formed in the ink container; and wherein the liquid-quantity determining device measures again the time periods each necessary for counting the predetermined number of pulses while a carriage holding the ink-jet recording head is stopped, when the measurement is judged to be incorrect.

19. The liquid-quantity monitoring apparatus ac-cording to claim 18, wherein the liquid-quantity determining device measures again the time periods each necessary for counting the predetermined number of pulses while an ink jetting operation of the ink-jet recording head is stopped, when the measurement is judged to be incorrect.

20. The liquid-quantity monitoring apparatus according to claim 17, wherein the liquid is contained in an ink container for an ink-jet recording head, the piezoelectric device being combined with the ink container with at least a part of the vibrating unit thereof exposed to an ink chamber formed in the ink container; and wherein the liquid-quantity determining device measures again the time periods each necessary for counting the predetermined number of pulses while an ink jetting operation of the ink-jet recording head is stopped, when the measurement is judged to be incorrect.

21. The liquid-quantity monitoring apparatus according to claim 15, wherein the liquid-quantity determining device is capable of deciding whether or not a level of the liquid passed a position where the vibrating part is positioned, based on a change of a resonance frequency of the residual vibration signal that occurs when the level of the liquid passes the vibrating part.

22. A liquid consuming apparatus comprising:

the liquid-quantity monitoring apparatus according to claim 15;

a liquid container combined with the piezoelectric device of the liquid-quantity monitoring apparatus; and a liquid consuming unit that consumes a liquid supplied from the liquid container.

23. A computer readable recording medium storing a program to be executed by a computer system including at least one computer to realize functions of the liquid-quantity determining device of the liquid-quantity monitoring apparatus according to claim 15.

* * * * *